US008835425B2

(12) United States Patent
Gasser et al.

(10) Patent No.: US 8,835,425 B2
(45) Date of Patent: Sep. 16, 2014

(54) USE OF SELECTIVE GABA A α5 NEGATIVE ALLOSTERIC MODULATORS FOR THE TREATMENT OF CENTRAL NERVOUS SYSTEM CONDITIONS

(75) Inventors: Rodolfo Gasser, Zuzgen (CH); Maria-Clemencia Hernandez, Delémont (CH); Andrew Thomas, Binningen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/286,240

(22) Filed: Nov. 1, 2011

(65) Prior Publication Data
US 2012/0115839 A1    May 10, 2012

(30) Foreign Application Priority Data

Nov. 5, 2010  (EP) ................................. 10190267
Nov. 16, 2010 (EP) ................................. 10191396

(51) Int. Cl.
| | | |
|---|---|---|
| A61K 31/54 | (2006.01) | |
| A01N 43/16 | (2006.01) | |
| A61K 31/42 | (2006.01) | |
| A61K 31/5377 | (2006.01) | |
| A61K 31/541 | (2006.01) | |
| A61K 31/5517 | (2006.01) | |
| A61K 31/551 | (2006.01) | |
| A61K 31/444 | (2006.01) | |
| A61K 31/4439 | (2006.01) | |
| A61K 31/4985 | (2006.01) | |

(52) U.S. Cl.
CPC ......... *A61K 31/4439* (2013.01); *A61K 31/5377* (2013.01); *A61K 31/541* (2013.01); *A61K 31/5517* (2013.01); *A61K 31/551* (2013.01); *A61K 31/444* (2013.01); *A61K 31/4985* (2013.01)
USPC .......................... 514/222.8; 514/279; 514/379

(58) Field of Classification Search
USPC ........................................ 514/222.8, 279, 379
See application file for complete search history.

(56) References Cited

U.S. PATENT DOCUMENTS

| | | |
|---|---|---|
| 2004/0235844 A1 | 11/2004 | Goodacre |
| 2006/0084642 A1 | 4/2006 | Knust et al. |
| 2006/0084801 A1 | 4/2006 | Knust et al. |
| 2009/0143371 A1 | 6/2009 | Buettelmann et al. |
| 2010/0256127 A1 | 10/2010 | Buettelmann et al. |

FOREIGN PATENT DOCUMENTS

| | | |
|---|---|---|
| EP | 2298296 | 3/2011 |
| WO | 0242305 | 5/2002 |
| WO | 2006/045429 | 5/2006 |
| WO | 2006/045430 | 5/2006 |
| WO | 2010053127 | 5/2010 |
| WO | 2010127976 | 11/2010 |
| WO | 2010127978 | 11/2010 |

OTHER PUBLICATIONS

Kishnani PS et al. "The efficacy, safety, and tolerability of donepezil for the treatment of young adults with Down syndrome". Am J Med Genet Part A 149A: 1641-1654.*
The Australian Examination Report, issued on Mar. 17, 2014, in the corresponding Australian application No. 2011325190.
The English translation of the Chinese Office Action, issued on Jan. 20, 2014, in the corresponding Chinese application No. 20118005316.5.
The English Translation of the Korean Office Action, issued on Jun. 26, 2014, in the corresponding Korean application No. 2013-7014355.
Ballard et al., "RO4938581, a novel cognitive enhancer acting at GABAA alpha5 subunit-containing receptors," Psychopharmacology, vol. 202(1-3), pp. 207-223, Jan. 2009.

* cited by examiner

*Primary Examiner* — Renee Claytor

(57) ABSTRACT

The present invention relates to the pharmaceutical use of selective GABA A α5 negative allosteric modulators for the treatment, prevention and/or delay of progression of central nervous system (CNS) conditions related to excessive GABAergic inhibition in the brain.

3 Claims, 23 Drawing Sheets

(A)

(B)

TS Vehicle    CO Vehicle    TS 8581    CO 8581

(A)

(B)

TS Vehicle　　CO Vehicle　　TS 8581　　CO 8581

USE OF SELECTIVE GABA A α5 NEGATIVE ALLOSTERIC MODULATORS FOR THE TREATMENT OF CENTRAL NERVOUS SYSTEM CONDITIONS

PRIORITY TO RELATED APPLICATION(S)

This application claims the benefit of European Patent Application No. 10190267.4, filed Nov. 5, 2010 and European Patent Application No. 10191396.0, filed Nov. 16, 2010, which is hereby incorporated by reference in its entirety.

BACKGROUND OF THE INVENTION

Down syndrome (DS), caused by triplication of chromosome 21, is the most frequent genetic cause of intellectual disability, with a prevalence of about one in 650-1000 live births worldwide [Bittles A H et al., Eur J Public Health (2007) 17(2):221-225]. Even though the etiology of the cognitive deficit in DS remains uncertain, cellular and anatomical abnormalities in the prenatal and perinatal forebrain and cerebellum suggest that early brain development is altered in individuals with DS. Similar central nervous system (CNS) abnormalities have been described in mouse models of DS. In particular, the Ts65Dn mouse, the most widely used model of DS, has abnormal forebrain and cerebellar development, defects in synapse formation and neurophysiology, and behavioral deficits.

Recent studies have suggested that the major functional defect in the postnatal Ts65Dn brain may be an imbalance between excitation and inhibition, e.g. a decreased numbers of excitatory synapses and a relative increase in inhibitory synaptic markers in the cortex and hippocampus. Further studies suggest that increased inhibitory synaptic drive may be a general physiological phenotype in the Ts65Dn forebrain.

There is currently no therapeutic option available for the treatment of cognitive deficit in people with DS. It has now been found, that inhibition of GABA A receptor function represents an attractive mechanism to treat cognitive impairment in DS.

The GABA A receptor regulating a chloride channel is the predominant inhibitory neurotransmitter receptor in the mammalian central nervous system and has been widely used as a target for neuromodulatory drugs. Many compounds in clinical use such as anxiolytics, sedatives, hypnotics or antiepileptics increase GABA A receptor activation via the allosteric benzodiazepine (BZD) binding site. Such compounds have been termed "BZD site receptor agonists." BZD binding site ligands producing the opposite effect, i.e., decreasing receptor activation, are called "BZD site receptor inverse agonists." "BZD site receptor antagonists" are ligands which bind to the receptor without modulating its function but which block the activity of both agonists and inverse agonists [Haefely W E, Eur Arch Psychiatry Neurol Sci (1989) 238: 294-301]. BZD receptor inverse agonists have so far only been tested in animal behavior experiments and in a very few exploratory human studies. The results showed beneficial activity, however, further development of the compounds that entered the clinic was prevented by anxiogenic effects, possibly resulting from the lack of selectivity shown by these agents for specific BZD receptor subtypes.

Non-selective antagonists, also called channel blockers, of the GABA A receptors (e.g. picrotoxin or PTZ) increase the risk of convulsions most likely through their actions on GABA A α1, α2, and α3 subunit containing receptors and, therefore, cannot be safely used in people with DS. It is hence a prerequisite that suitable GABA A receptor inhibitors are selective for the receptor subtype mainly involved in memory formation.

GABA A receptors are pentamers mostly consisting of two α, two β and a γ subunit. Several gene products are available for each of the subunits giving rise to a large number of receptor variants. The importance of different α subunit subtypes has been elucidated by the generation of transgenic mice lacking the normal diazepam sensitivity of the α1, α2, α3 or α5 subunit (α4 and α6 are diazepam insensitive). The results suggest that α1 is responsible for the sedative effects and α2 and perhaps α3 for the anxiolytic effects of BZD receptor ligand agonists [Löw K et al., Science (2000) 290 (5489):131-134; Möhler H, Cell Tissue Res (2006) 326(2): 505-516]. The consequences of a modified pharmacology of the α5 subunit are less evident, but reduced or no expression of the subunit could be associated with facilitated cognition in hippocampal-dependent tasks and importantly, no effects on anxiety or proconvulsant paradigms. This is in line with the preferential localization of α5 subunits in the hippocampus.

SUMMARY OF THE INVENTION

The present invention provides methods for the treatment, prevention and/or delay of progression of central nervous system (CNS) conditions related to excessive GABAergic inhibition in the cortex and hippocampus which comprises administering selective GABA A α5 negative allosteric modulators. More particularly, the present invention provides methods for the treatment, prevention and/or delay of progression of CNS conditions caused by neurodevelopmental defects which result in excessive GABAergic inhibition in the cortex and hippocampus, wherein the CNS condition is selected from cognitive deficits in Down Syndrome, in autism, in neurofibromatosis type I, or for the recovery after stroke which comprises administering selective GABA A α5 negative allosteric modulators.

In particular, the present invention provides methods for the treatment, prevention and/or delay of progression of CNS conditions, which comprises administering selective GABA A α5 negative allosteric modulators wherein the selective GABA A α5 negative allosteric modulator is a compound of formula (I) and/or a compound of formula (II)

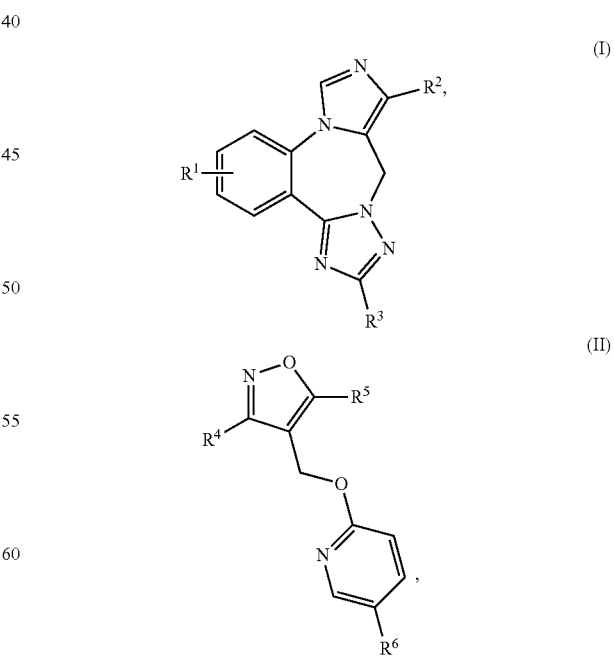

wherein $R^1$, $R^2$, $R^3$, $R^4$, $R^5$, and $R^6$ are as defined herein, or a pharmaceutically acceptable salt thereof.

It is therefore hypothesized that a BZD site ligand with inverse agonism selective for GABA A α5 subunit-containing receptors should enhance cognitive function without anxiogenic and proconvulsant side effects.

Selectivity of a BZD site ligand can be achieved by different affinities to GABA A receptor subtypes ("binding selectivity"). Alternatively, in the case of similar subtype affinities, different degrees of receptor modulation ("functional selectivity") can be attempted, i.e., inverse agonism at GABA A α5 receptor subtype and no activity at other subtypes. A compound may also have a combination of both binding and functional selectivity although so far this is rare. A number of compounds described as being active as inverse agonists at the GABA A α5 subunit-containing receptors have recently been synthesized [WO 2006/045429, WO 2006/045430, WO 2007/042421, WO 2009/071476]. Certain of these compounds have a beneficial pharmacological profile with excellent binding and functional selectivity for the GABA A α5 subunit-containing receptors. Results confirm the hypothesis that compounds with such a pharmacological profile can improve cognitive function without CNS-mediated adverse effects including anxiety and/or convulsions [Ballard T M et al., *Psychopharmacology*, (2009) 202:207-223].

The pharmaceutically active compounds used in present invention are molecules combining both binding and functional selectivity at the GABA A α5 subunit-containing receptors that improve cognition. Importantly, pharmaceutically active compounds used in present invention lack anxiogenic or proconvulsant effects at the exposures tested in toxicology studies.

Selective GABA A α5 negative allosteric modulators have procognitive effects on several animal models but are not anxiogenic or proconvulsant. The active pharmaceutical compounds used in present invention were chronically administered to Ts65Dn and control (euploid) mice and a battery of behavioral tests, including the assessment of sensorimotor abilities, anxiety and cognition was performed. The active pharmaceutical compounds used in present invention improved Ts65Dn, but not control, mice performance in the Morris water maze and did not affect the sensorimotor abilities, general activity, motor coordination or anxiety of Ts65Dn or control mice. Plasma concentrations of active pharmaceutical compounds from blood samples taken from treated Ts65Dn and control mice relate to levels of GABA A α5 receptor occupancy of 25-75% from an in vivo binding mimic study. Importantly, these experiments confirmed the selective occupancy of brain GABA A α5 receptors and reinforce the notion that dual binding and functional selectivity offers an ideal profile for cognition-enhancing effects without the unwanted side effects associated with activity at other GABA A receptor subtypes.

Interestingly it was revealed that chronic administration of the active pharmaceutical compounds used in present invention:

1. did not modify any of the sensorimotor abilities tested in Ts65Dn or control mice;
2. did not affect motor coordination in the Rotarod test;
3. did not modify spontaneous locomotor activity in the home-cage during the light or the dark phase of the cycle;
4. in the Open Field test did not modify the anxiety or locomotor activity of Ts65Dn and control mice;
5. in the Hole Board test reduced the hyperactivity found in vehicle-treated Ts65Dn mice;
6. in the Morris water maze it improved Ts65Dn mice performance during the acquisition and the cued sessions.

It was further found that the active pharmaceutical compounds used in present invention:

a) reverse the spatial learning deficits in Nf1+/− mutant mice under conditions in which such compounds do not enhance learning in control mice;
b) do not affect the performance of Nf1+/− mice under conditions that occlude their behavioral deficits;
c) do not affect motor learning in the rotarod test in Nf1+/− and control mice;
d) are useful as potential treatments for the cognitive deficits associated with NF1.

ABBREVIATIONS

Figure 1:
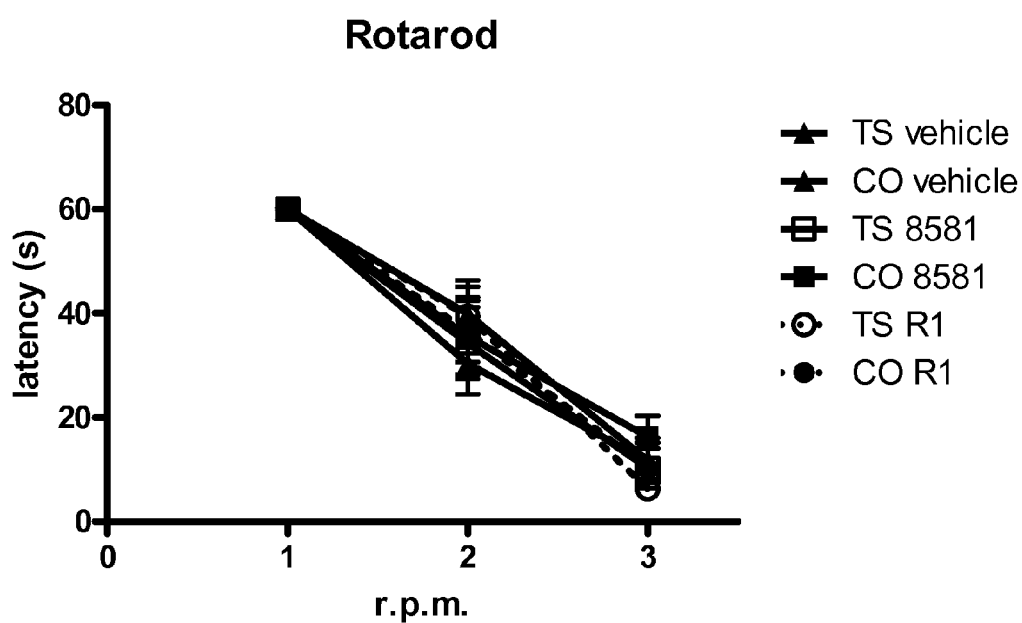
FIG. 1. Mean±S.E.M. of the latency of 8581-, R1- and vehicle-treated Ts65Dn and control mice to fall from the rotarod at different constant speeds.

ANOVA=analysis of variance
BZD=benzodiazepine
CNS=central nervous system
CO=control
DS=Down Syndrome
F=F-test value
GABA=gamma-aminobutyric acid
i.p.=intraperitoneal
LTP=long-term potentiation
MANOVA=multivariate analysis of variance
MWM=Morris Water maze
p=probability
p.o.=peroral
S.E.M.=standard error of the mean
TS=Ts65Dn
veh=vehicle

BRIEF DESCRIPTION OF THE TABLES

Table 1. Experimental groups of animals used in this invention for examples 1 to 6.

Table 2a. Binding affinities and binding selectivities of active pharmaceutical compounds used in this invention.

Table 2b. Modulation of GABA A receptor subtypes expressed in *Xenopus* oocytes by active pharmaceutical compounds. Effect at human GABA A α5 receptors: % change of a submaximal (EC10) response to GABA determined at 30×Ki value from the flumazenil binding assay. Effect at human GABA A α1, α2 and α3 receptors: % change of a submaximal (EC10) response to GABA determine at 3 μM or at 30×Ki value from the flumazenil binding assay, if Ki was below 0.1 μM.

Table 3. Sensorimotor Test Battery (Mean Scores±S.E.M.) of 8581-, R1- and vehicle-treated Ts65Dn and control mice.

Table 4. Hole Board test results (Mean Scores±S.E.M.) of R1-, 8581- and vehicle-treated Ts65Dn and control mice. \*\*: $p<0.01$ Ts65Dn vs. Control Table 5. 8581 concentration in serum (ng/ml) of Nf1+/− and control mice 0.5, 3, 7, and 24 hours after i.p. injection

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

The nomenclature used in this application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein can be appended to form chemically-relevant combinations, such as e.g. "heterocycloalkyl-aryl", "haloalkyl-heteroaryl", "arylalkyl-heterocycloalkyl", or "alkoxy-alkyl." The last member of the combination is a radical which is substituted by the other members of the combination in inverse order.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance may, but need not, occur and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) used in this invention" and "compound(s) used present invention" refers to compounds of formula (I) or (II) and stereoisomers, tautomers, solvates, and salts (e.g., pharmaceutically acceptable salts) thereof.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid. The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

The terms "halo," "halogen," and "halide" are used interchangeably herein and denote fluoro, chloro, bromo, or iodo. Particularly, halo refers to F, Cl or Br, most particularly to F.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, or tert-butyl. Particularly, alkyl refers to methyl or isopropyl, most particularly to methyl.

The term "alkoxy" denotes a group of the formula —O—R', wherein R' is an alkyl group. Examples of alkoxy moieties include methoxy, ethoxy, isopropoxy, and tert-butoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particularly, haloalkyl refers to monofluoromethyl and difluoromethyl.

The term "hydroxyalkyl" denotes an alkyl group wherein at least one of the hydrogen atoms of the alkyl group has been replaced by a hydroxy group. Examples of hydroxyalkyl include hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two rings having two ring atoms in common, i.e. the bridge separating the two rings is either a single bond or a chain of one or two ring atoms. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Heterocycloalkyl can optionally be substituted as described herein. Particularly, heterocycloalkyl refers to morpholinyl, thiomorpholinyl, dioxothiomorpholinyl, 2-oxa-6-aza-spiro[3.3]hept-6-yl, pyrrolidinyl, and oxopyrrolidinyl. Most particularly, heterocycloalkyl refers to morpholinyl, thiomorpholinyl, or dioxothiomorpholinyl.

The term "heterocycloalkylalkyl" denotes an alkyl group wherein at least one of the hydrogen atoms of the alkyl group is replaced by a heterocycloalkyl group. Examples of heterocycloalkylalkyl include pyrrolidinyl-methyl, and pyrrolidinyl-methyl.

The term "aryl" denotes a monovalent aromatic carbocyclic mono- or bicyclic ring system comprising 6 to 10 carbon ring atoms. Examples of aryl moieties include phenyl and naphthyl. Aryl can optionally be substituted as described herein. Particular aryl is phenyl, and monofluoro-phenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, carbazolyl, or acridinyl. Heteroaryl can optionally be substituted as described herein. Particularly, heteroaryl refers to pyridinyl, monofluoropyridinyl, and 5,6-Dihydro-8H-[1,2,4]triazolo[4,3-a]pyrazin-7-yl, most particularly to pyridinyl, and monofluoropyridinyl.

The term "oxo" denotes a divalent oxygen atom =O.

The term "active pharmaceutical ingredient" (or "API") denotes the compound in a pharmaceutical composition that has a particular biological activity.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "pharmaceutical composition" (or "composition") denotes a mixture or solution comprising a therapeutically effective amount of an active pharmaceutical ingredient together with pharmaceutically acceptable excipients to be administered to a mammal, e.g., a human in need thereof.

The term "modulator" denotes a molecule that interacts with a target receptor. The interactions include e.g. agonistic, antagonistic, or inverse agonistic activity.

The term "inhibitor" denotes a compound which competes with, reduces or prevents the binding of a particular ligand to particular receptor or which reduces or prevents the inhibition of the function of a particular protein.

The term "agonist" denotes a compound that has affinity to a receptor binding site and which enhances the activity of the receptor-mediated response as defined e.g. in Goodman and Gilman's "*The Pharmacological Basis of Therapeutics*, 7th ed." in page 35, Macmillan Publ. Company, Canada, 1985. A "full agonist" effects a full response whereas a "partial agonist" effects less than full activation even when occupying the total receptor population. An "inverse agonist" produces an effect opposite to that of an agonist by binding to the same agonist binding site, or reduces the effect of an agonist by binding at a different allosteric binding site.

The term "antagonist" denotes a compound that diminishes or prevents the action of another compound or receptor site as defined e.g. in Goodman and Gilman's "*The Pharmacological Basis of Therapeutics*, 7th ed." in page 35, Macmillan Publ. Company, Canada, 1985. In particular, antagonists refers to a compound that attenuates the effect of an agonist. A "competitive antagonist" binds to the same site as the agonist but does not activate it, thus blocks the agonist's action. A "non-competitive antagonist" binds to an allosteric (non-agonist) site on the receptor to prevent activation of the receptor. A "reversible antagonist" binds non-covalently to the receptor, therefore can be "washed out." An "irreversible antagonist" binds covalently to the receptor and cannot be displaced by either competing ligands or washing.

The term "allosteric modulator" denotes a compound that binds to a receptor at a site distinct from the agonist binding site (an "allosteric site"). It induces a conformational change in the receptor, which alters the affinity of the receptor for the endogenous ligand or agonist. "Positive allosteric modulators" increase the affinity, whilst "negative allosteric modulators" (NAM) decrease the affinity and hence decrease the activity of a receptor indirectly. In present invention, a negative allosteric modulator particularly binds to the benzodiazepine binding site with inverse agonism selective for GABA A α5 subunit-containing receptor.

The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "submaximal effective concentration" (EC10) denotes the concentration of a particular compound required for obtaining 10% of the maximum of a particular effect.

The term "binding selectivity" denotes the ratio between the binding affinity of a particular compound to two or more different receptor subtypes. A particular compound is characterized as "binding selective" if its binding selectivity is 10 or more, more particularly if its binding selectivity is 20 or more, most particularly if its binding selectivity is 50 or more.

The term "functional selectivity" denotes the different degrees of modulation by a particular compound at different receptor subtypes, e.g. by acting as an inverse agonist at one particular receptor subtype whereas acting as an antagonist at another receptor subtype. In present invention, a compound is particularly functional selective if it acts as inverse agonist at GABA A α5β3γ2 receptor subtype by reducing the effect of GABA by more than 30% while affecting the other GABA A receptor subtypes by less than 15%, particularly by less than 10%.

The terms "condition", "defect", "disability", "disorder", "disease" or "disease state" are used interchangeably to denote any disease, condition, symptom, disorder or indication.

The term "neurodevelopmental defect" denotes a disorder of neural development, wherein growth and development of the brain or central nervous system has been impaired (Reynolds C R et al., *Handbook of neurodevelopmental and genetic disorders in children* (1999) Guilford Press, NY).

The term "GABAergic inhibition" refers to GABA mediated neurotransmission which is inhibitory to mature neurons in vertebrates (Bernard C et al., *Epilepsia* (2000) 41(S6): S90-S95).

The term "excessive GABAergic inhibition" refers to increased GABA-mediated neurotransmission which results in disruption of excitatory/inhibitory (E/I) circuit balance in favor of inhibition (Kleschevnikov A. M. et al., *J. Neurosci.* (2004) 24:8153-8160).

The term "cognitive deficit" or "cognitive impairment" describes any characteristic that acts as a barrier to cognitive performance. The term denotes deficits in global intellectual performance, such as mental retardation, it denotes specific deficits in cognitive abilities (learning disorders, dyslexia), or it denotes drug-induced memory impairment. Cognitive deficits can be congenital or caused by environmental factors such as brain injuries, neurological disorders, or mental illness. The term "cognitive deficit in Down Syndrome" or "cognitive impairment in Down Syndrome" denotes cognitive deficits in subjects exhibiting a triplication of chromosome 21, in particular abnormalities in learning, memory, and language that lead to mild to profound impairment in intellectual functioning in such subjects.

The term "intellectual disability" (ID) or "mental retardation" denotes an early onset cognitive impairment expressed by a significantly reduced ability to understand new or complex information, to learn new skills, with a reduced ability to cope independently, which started before adulthood, with a lasting effect on development.

The term "procognitive" describes any characteristic that reduces or reverts conditions such as mental confusion, disorientation, delirium or cognitive deficits or that improves cognition.

The term "neurofibromatosis type 1" (NF1) denotes a disorder that is caused by a mutation of a gene on chromosome 17 which encodes a protein known as neurofibromin relevant in intracellular signaling (Cui Y et al., Cell (2008) 135:549-60).

The term "autism" denotes a disorder of neural development characterized by impaired social interaction and communication, and by restricted and repetitive behavior (American Psychiatric Association Inc., Diagnostic and Statistical Manual of Mental Disorders (DSM-IV-TR) (2000) 4th ed.).

The term "stroke" is the rapidly developing loss of brain function(s) due to disturbance in the blood supply to the brain. This can be due to ischemia (lack of blood flow) caused by blockage (thrombosis, arterial embolism), or a hemorrhage (Sims N R et al, Biochimica et Biophysica Acta (2009) 1802 (1):80-91).

The term "recovery after stroke" refers to the ability to restore impaired brain function after stroke (Dimyan M. A. et al., Nat Rev Neurol. (2011) 7(2):76-85).

The term "treating" or "treatment" of a disease state includes (1) preventing the disease state, i.e. causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgement of the attending medical or veterinary practitioner, and other factors.

The term "subject" or "patient" denotes an animal, more particularly a vertebrate. In certain embodiments, the vertebrate is a mammal Mammals include humans, non-human primates such as chimpanzees and other apes and monkey species, farm animals such as cattle, horses, sheep, goats, and swine, domestic animals such as rabbits, dogs, and cats, laboratory animals including rodents, such as rats, mice, and guinea pigs. In certain embodiments, a mammal is a human. The term subject does not denote a particular age or sex.

In detail, the present invention provides the use of a GABA A α5 negative allosteric modulator for the treatment, prevention and/or delay of progression of central nervous system (CNS) conditions caused by neurodevelopmental defects which result in excessive GABAergic inhibition in the cortex and hippocampus.

In a particular embodiment, the invention provides the use of a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from cognitive deficits in Down Syndrome, in autism, in neurofibromatosis type I, or after stroke.

In a particular embodiment, the invention provides the use of a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from cognitive deficits in Down Syndrome.

In a particular embodiment, the invention provides the use of a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from cognitive deficits in autism.

In a particular embodiment, the invention provides the use of a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from cognitive deficits in neurofibromatosis type I.

In a particular embodiment, the invention provides the use of a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from cognitive deficits after stroke.

In a particular embodiment, the invention provides the use of a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from intellectual disability.

In a particular embodiment, the invention provides the use of a GABA A α5 negative allosteric modulator, wherein the GABA A α5 negative allosteric modulator is a ligand to a BZD binding site and is acting as inverse agonist at GABA A α5 subunit-containing receptors.

In a particular embodiment, the invention provides the use of a GABA A α5 negative allosteric modulator, wherein the GABA A α5 negative allosteric modulator is a ligand to the BZD binding site of the GABA A receptor and is acting as inverse agonist at the GABA A α5β3γ2 receptor subtype.

In a particular embodiment, the invention provides the use of a GABA A α5 negative allosteric modulator, wherein the GABA A α5 negative allosteric modulator has binding selectivity at GABA A α5 subunit-containing receptors.

In a particular embodiment, the invention provides the use of a GABA A α5 negative allosteric modulator, wherein the GABA A α5 negative allosteric modulator has functional selectivity at GABA A α5 subunit-containing receptors.

In a particular embodiment, the invention provides the use of a GABA A α5 negative allosteric modulator, wherein the GABA A α5 negative allosteric modulator is binding to human GABA A α5β3γ2 receptor subtype with a binding selectivity of a factor of 10 or more as compared to binding affinities to human GABA A α1β2/3γ2, α2β2/3γ2 and α3β2/3γ2 receptor subtypes.

In a particular embodiment, the invention provides the use of a GABA A α5 negative allosteric modulator, wherein the GABA A α5 negative allosteric modulator has binding selectivity at GABA A α5 subunit-containing receptors.

In a particular embodiment, the invention provides the use of a GABA A α5 negative allosteric modulator, wherein the GABA A α5 negative allosteric modulator exhibits a functional selectivity by acting as inverse agonist at human GABA A α5β3γ2 receptor subtype by reducing the effect of GABA by more than 30% and in addition affecting the effect of GABA at human GABA A α1β2/3γ2, α2β2/3γ2 and α3β2/3γ2 receptor subtypes by less than 15%.

In a particular embodiment, the invention provides the use of a GABA A α5 negative allosteric modulator, wherein the GABA A α5 negative allosteric modulator is selected from a compound of formula (I) or a compound of formula (II)

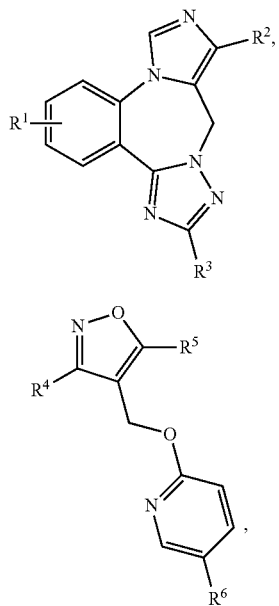

wherein
$R^1$ is hydrogen, halo, alkyl, haloalkyl, or cyano;
$R^2$ is hydrogen, halo, alkyl, haloalkyl, or cyano;
$R^3$ is hydrogen, alkyl, or heterocycloalkylalkyl, wherein heterocycloalkylalkyl is optionally substituted with one or more hydroxy, oxo, alkyl, alkoxy, haloalkyl, hydroxyalkyl, halo, or cyano;
$R^4$ is aryl or heteroaryl, each optionally substituted by one, two or three halo;
$R^5$ is hydrogen, alkyl, haloalkyl or hydroxyalkyl;
$R^6$ is —C(O)—NR$^7$R$^8$
$R^7$ is hydrogen;
$R^8$ is alkyl;
or $R^7$ and $R^8$ together with the nitrogen to which they are bound form a heterocycloalkyl, or a heteroaryl, each optionally substituted with one or more hydroxy, oxo, alkyl, alkoxy, haloalkyl, hydroxyalkyl, halo, or cyano;
or a pharmaceutically acceptable salt thereof.

In a particular embodiment, the invention provides the use of a GABA A α5 negative allosteric modulator, wherein the GABA A α5 negative allosteric modulator is selected from a compound of formula (I) wherein
$R^1$ is hydrogen, halo, alkyl, haloalkyl, or cyano;
$R^2$ is hydrogen, halo, alkyl, haloalkyl, or cyano;
$R^3$ is hydrogen, alkyl, or heterocycloalkylalkyl, wherein heterocycloalkylalkyl is optionally substituted with one or more hydroxy, oxo, alkyl, alkoxy, haloalkyl, hydroxyalkyl, halo, or cyano;
or a pharmaceutically acceptable salt thereof.

In a particular embodiment, the invention provides the use of a GABA A α5 negative allosteric modulator, wherein the GABA A α5 negative allosteric modulator is selected from a compound of formula (I) wherein
$R^1$ is hydrogen, halo, haloalkyl, or cyano;
$R^2$ is halo, or haloalkyl;
$R^3$ is hydrogen, alkyl, or heterocycloalkylalkyl substituted with one oxo;
or a pharmaceutically acceptable salt thereof.

In a particular embodiment, the invention provides the use of a GABA A α5 negative allosteric modulator, wherein the GABA A α5 negative allosteric modulator is selected from:
3-Fluoro-10-fluoromethyl-9H-imidazo[1,5-a][1,2,4]triazolo[1,5-d][1,4]benzodiazepine;
3-Bromo-10-difluoromethyl-9H-imidazo[1,5-a][1,2,4]triazolo[1,5-d][1,4]benzodiazepine;
3-Cyano-10-difluoromethyl-9H-imidazo[1,5-a][1,2,4]triazolo[1,5-d][1,4]benzodiazepine;
10-Difluoromethyl-9H-imidazo[1,5-a][1,2,4]triazolo[1,5-d][1,4]benzodiazepine;
3-Chloro-10-fluoromethyl-6-methyl-9H-imidazo[1,5-a][1,2,4]triazolo[1,5-d][1,4]benzodiazepine;
10-Chloro-9H-imidazo[1,5-a][1,2,4]triazolo[1,5-d][1,4]benzodiazepine;
3,10-Dichloro-9H-imidazo[1,5-a][1,2,4]triazolo[1,5-d][1,4]benzodiazepine;
10-Chloro-3-cyano-6-methyl-9H-imidazo[1,5-a][1,2,4]triazolo[1,5-d][1,4]benzodiazepine;
10-Chloro-3-difluoromethyl-9H-imidazo[1,5-a][1,2,4]triazolo[1,5-d][1,4]benzodiazepine;
3-Bromo-10-chloro-6-methyl-9H-imidazo[1,5-a][1,2,4]triazolo[1,5-d][1,4]benzodiazepine;
10-Bromo-3-fluoro-9H-imidazo[1,5-a][1,2,4]triazolo[1,5-d][1,4]benzodiazepine;
3-Bromo-10-methyl-6-(2-oxo-pyrrolidin-1-ylmethyl)-9H-imidazo[1,5-a][1,2,4]triazolo[1,5-d][1,4]benzodiazepine;
or a pharmaceutically acceptable salt thereof.

In a particular embodiment, the invention provides the use of a GABA A α5 negative allosteric modulator, wherein the GABA A α5 negative allosteric modulator is 3-Bromo-10-difluoromethyl-9H-imidazo[1,5-a][1,2,4]triazolo[1,5-d][1,4]benzodiazepine; or a pharmaceutically acceptable salt thereof.

In a particular embodiment, the invention provides the use of a GABA A α5 negative allosteric modulator, wherein the GABA A α5 negative allosteric modulator is not 3-Bromo-10-difluoromethyl-9H-imidazo[1,5-a][1,2,4]triazolo[1,5-d][1,4]benzodiazepine; or a pharmaceutically acceptable salt thereof.

In a particular embodiment, the invention provides the use of a GABA A α5 negative allosteric modulator, wherein the GABA A α5 negative allosteric modulator is selected from a compound of formula (II) wherein
$R^4$ is aryl or heteroaryl, each optionally substituted by one, two or three halo;
$R^5$ is hydrogen, alkyl, haloalkyl or hydroxyalkyl;
$R^6$ is —C(O)—NR$^7$R$^8$;
$R^7$ is hydrogen;
$R^8$ is alkyl;
or $R^7$ and $R^8$ together with the nitrogen to which they are bound form a heterocycloalkyl, or a heteroaryl, each optionally substituted with one or more hydroxy, oxo, alkyl, alkoxy, haloalkyl, hydroxyalkyl, halo, or cyano;
or a pharmaceutically acceptable salt thereof.

In a particular embodiment, the invention provides the use of a GABA A α5 negative allosteric modulator, wherein the GABA A α5 negative allosteric modulator is selected from a compound of formula (II) wherein
R⁴ is aryl or heteroaryl, each optionally substituted by one halo;
R⁵ is alkyl;
R⁶ is C(O)—NR⁷R⁸;
R⁷ is hydrogen and R⁸ is alkyl;
or R⁷ and R⁸ together with the nitrogen to which they are bound form a heterocycloalkyl optionally substituted with one or two oxo, or form a heteroaryl;
or a pharmaceutically acceptable salt thereof.

In a particular embodiment, the invention provides the use of a GABA A α5 negative allosteric modulator, wherein the GABA A α5 negative allosteric modulator is selected from:
N-Isopropyl-6-(5-methyl-3-phenyl-isoxazol-4-ylmethoxy)-nicotinamide;
(5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone;
[6-(5-Methyl-3-phenyl-isoxazol-4-ylmethoxy)-pyridin-3-yl]-(2-oxa-6-aza-spiro[3.3]hept-6-yl)-methanone;
(1,1-Dioxo-1,6-thiomorpholin-4-yl)-{6-[3-(4-fluoro-phenyl)-5-methyl-isoxazol-4-ylmethoxy]-pyridin-3-yl}-methanone;
{6-[3-(4-Chloro-phenyl)-5-methyl-isoxazol-4-ylmethoxy]-pyridin-3-yl}-morpholin-4-yl-methanone;
[6-(5-Methyl-3-pyridin-2-yl-isoxazol-4-ylmethoxy)-pyridin-3-yl]-morpholin-4-yl-methanone;
6-[3-(5-Fluoro-pyridin-2-yl)-5-methyl-isoxazol-4-ylmethoxy]-isopropyl-nicotinamide;
(1,1-Dioxo-1,6-thiomorpholin-4-yl)-{6-[3-(5-fluoro-pyridin-2-yl)-5-methyl-isoxazol-4-ylmethoxy]-pyridin-3-yl}-methanone;
{6-[3-(5-Chloro-pyridin-2-yl)-5-methyl-isoxazol-4-ylmethoxy]-pyridin-3-yl}-thiomorpholin-4-yl-methanone;
or a pharmaceutically acceptable salt thereof.

In a particular embodiment, the invention provides the use of a GABA A α5 negative allosteric modulator, wherein the GABA A α5 negative allosteric modulator is N-Isopropyl-6-(5-methyl-3-phenyl-isoxazol-4-ylmethoxy)-nicotinamide; or a pharmaceutically acceptable salt thereof.

In a particular embodiment, the invention provides the use of a GABA A α5 negative allosteric modulator, wherein the GABA A α5 negative allosteric modulator is (5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone; or a pharmaceutically acceptable salt thereof.

In a particular embodiment, the invention provides the use of a GABA A α5 negative allosteric modulator, wherein the GABA A α5 negative allosteric modulator is [6-(5-Methyl-3-phenyl-isoxazol-4-ylmethoxy)-pyridin-3-yl]-(2-oxa-6-aza-spiro[3.3]hept-6-yl)-methanone; or a pharmaceutically acceptable salt thereof.

In a particular embodiment, the invention provides the use of a GABA A α5 negative allosteric modulator, wherein the GABA A α5 negative allosteric modulator is (1,1-Dioxo-1,6-thiomorpholin-4-yl)-{6-[3-(4-fluoro-phenyl)-5-methyl-isoxazol-4-ylmethoxy]-pyridin-3-yl}-methanone; or a pharmaceutically acceptable salt thereof.

In a particular embodiment, the invention provides the use of a GABA A α5 negative allosteric modulator, wherein the GABA A α5 negative allosteric modulator is {6-[3-(4-Chloro-phenyl)-5-methyl-isoxazol-4-ylmethoxy]-pyridin-3-yl}-morpholin-4-yl-methanone; or a pharmaceutically acceptable salt thereof In a particular embodiment, the invention provides the use of a GABA A α5 negative allosteric modulator, wherein the GABA A α5 negative allosteric modulator is [6-(5-Methyl-3-pyridin-2-yl-isoxazol-4-ylmethoxy)-pyridin-3-yl]-morpholin-4-yl-methanone; or a pharmaceutically acceptable salt thereof.

In a particular embodiment, the invention provides the use of a GABA A α5 negative allosteric modulator, wherein the GABA A α5 negative allosteric modulator is 6-[3-(5-Fluoro-pyridin-2-yl)-5-methyl-isoxazol-4-ylmethoxy]-isopropyl-nicotinamide; or a pharmaceutically acceptable salt thereof.

In a particular embodiment, the invention provides the use of a GABA A α5 negative allosteric modulator, wherein the GABA A α5 negative allosteric modulator is (1,1-Dioxo-1,6-thiomorpholin-4-yl)-{6-[3-(5-fluoro-pyridin-2-yl)-5-methyl-isoxazol-4-ylmethoxy]-pyridin-3-yl}-methanone; or a pharmaceutically acceptable salt thereof.

In a particular embodiment, the invention provides the use of a GABA A α5 negative allosteric modulator, wherein the GABA A α5 negative allosteric modulator is {6-[3-(5-Chloro-pyridin-2-yl)-5-methyl-isoxazol-4-ylmethoxy]-pyridin-3-yl}-thiomorpholin-4-yl-methanone; or a pharmaceutically acceptable salt thereof.

In a particular embodiment, the invention provides the use of a GABA A α5 negative allosteric modulator, wherein the GABA A α5 negative allosteric modulator is used separately, sequentially or simultaneously in combination with a second active pharmaceutical compound.

In a particular embodiment, the invention provides a method for the treatment, prevention and/or delay of progression of central nervous system (CNS) conditions caused by neurodevelopmental defects which result in excessive GABAergic inhibition in the cortex and hippocampus in a subject in need of such treatment, which comprises administering to said subject a therapeutically effective amount of a GABA A α5 negative allosteric modulator as described herein in a pharmaceutically acceptable form.

In a particular embodiment, the invention provides a method for the treatment, prevention and/or delay of progression of central nervous system (CNS) conditions, wherein said CNS condition is selected from cognitive deficits in Down Syndrome, in a subject in need of such treatment, which comprises administering to said subject a therapeutically effective amount of a GABA A α5 negative allosteric modulator as described herein in a pharmaceutically acceptable form.

In a particular embodiment, the invention provides a method for the treatment, prevention and/or delay of progression of central nervous system (CNS) conditions, wherein said CNS condition is selected from cognitive deficits in autism, in a subject in need of such treatment, which comprises administering to said subject a therapeutically effective amount of a GABA A α5 negative allosteric modulator as described herein in a pharmaceutically acceptable form.

In a particular embodiment, the invention provides a method for the treatment, prevention and/or delay of progression of central nervous system (CNS) conditions, wherein said CNS condition is selected from cognitive deficits in neurofibromatosis type I, in a subject in need of such treatment, which comprises administering to said subject a therapeutically effective amount of a GABA A α5 negative allosteric modulator as described herein in a pharmaceutically acceptable form.

In a particular embodiment, the invention provides a method for the treatment, prevention and/or delay of progression of central nervous system (CNS) conditions, wherein said CNS condition is selected from cognitive deficits after stroke, in a subject in need of such treatment, which comprises administering to said subject a therapeutically effective amount of a GABA A α5 negative allosteric modulator as described herein in a pharmaceutically acceptable form.

In a particular embodiment, the invention provides a method for the treatment, prevention and/or delay of progression of central nervous system (CNS) conditions, wherein said CNS condition is selected from intellectual disability, in a subject in need of such treatment, which comprises administering to said subject a therapeutically effective amount of a GABA A α5 negative allosteric modulator as described herein in a pharmaceutically acceptable form.

In a particular embodiment, the invention provides a pharmaceutical composition comprising a GABA A α5 negative allosteric modulator as described herein in a pharmaceutically acceptable form for the treatment, prevention and/or delay of progression of central nervous system (CNS) conditions caused by neurodevelopmental defects which result in excessive GABAergic inhibition in the cortex and hippocampus.

In a particular embodiment, the invention provides a pharmaceutical composition comprising a GABA A α5 negative allosteric modulator as described herein in a pharmaceutically acceptable form for the treatment, prevention and/or delay of progression of central nervous system (CNS) conditions, wherein said CNS condition is selected from cognitive deficits in Down Syndrome.

In a particular embodiment, the invention provides a pharmaceutical composition comprising a GABA A α5 negative allosteric modulator as described herein in a pharmaceutically acceptable form for the treatment, prevention and/or delay of progression of central nervous system (CNS) conditions, wherein said CNS condition is selected from cognitive deficits in autism.

In a particular embodiment, the invention provides a pharmaceutical composition comprising a GABA A α5 negative allosteric modulator as described herein in a pharmaceutically acceptable form for the treatment, prevention and/or delay of progression of central nervous system (CNS) conditions, wherein said CNS condition is selected from cognitive deficits in neurofibromatosis type I.

In a particular embodiment, the invention provides a pharmaceutical composition comprising a GABA A α5 negative allosteric modulator as described herein in a pharmaceutically acceptable form for the treatment, prevention and/or delay of progression of central nervous system (CNS) conditions, wherein said CNS condition is selected from cognitive deficits after stroke.

In a particular embodiment, the invention provides a pharmaceutical composition comprising a GABA A α5 negative allosteric modulator as described herein in a pharmaceutically acceptable form for the treatment, prevention and/or delay of progression of central nervous system (CNS) conditions, wherein said CNS condition is selected from intellectual disability.

In a particular embodiment, the invention provides the use of a GABA A α5 negative allosteric modulator as described herein for the preparation of medicaments for the treatment, prevention and/or delay of progression of central nervous system (CNS) conditions caused by neurodevelopmental defects which result in excessive GABAergic inhibition in the cortex and hippocampus.

In a particular embodiment, the invention provides the use of a GABA A α5 negative allosteric modulator as described herein for the preparation of medicaments for the treatment, prevention and/or delay of progression of central nervous system (CNS) conditions, wherein said CNS condition is selected from cognitive deficits in Down Syndrome.

In a particular embodiment, the invention provides the use of a GABA A α5 negative allosteric modulator as described herein for the preparation of medicaments for the treatment, prevention and/or delay of progression of central nervous system (CNS) conditions, wherein said CNS condition is selected from cognitive deficits in autism.

In a particular embodiment, the invention provides the use of a GABA A α5 negative allosteric modulator as described herein for the preparation of medicaments for the treatment, prevention and/or delay of progression of central nervous system (CNS) conditions, wherein said CNS condition is selected from cognitive deficits in neurofibromatosis type I.

In a particular embodiment, the invention provides the use of a GABA A α5 negative allosteric modulator as described herein for the preparation of medicaments for the treatment, prevention and/or delay of progression of central nervous system (CNS) conditions, wherein said CNS condition is selected from cognitive deficits after stroke.

In a particular embodiment, the invention provides the use of a GABA A α5 negative allosteric modulator as described herein for the preparation of medicaments for the treatment, prevention and/or delay of progression of central nervous system (CNS) conditions, wherein said CNS condition is selected from intellectual disability.

In a particular embodiment, the invention provides a GABA A α5 negative allosteric modulator as described herein for the treatment, prevention and/or delay of progression of central nervous system (CNS) conditions caused by neurodevelopmental defects which result in excessive GABAergic inhibition in the cortex and hippocampus.

In a particular embodiment, the invention provides a GABA A α5 negative allosteric modulator as described herein for the treatment, prevention and/or delay of progression of central nervous system (CNS) conditions, wherein said CNS condition is selected from cognitive deficits in Down Syndrome.

In a particular embodiment, the invention provides a GABA A α5 negative allosteric modulator as described herein for the treatment, prevention and/or delay of progression of central nervous system (CNS) conditions, wherein said CNS condition is selected from cognitive deficits in autism.

In a particular embodiment, the invention provides a GABA A α5 negative allosteric modulator as described herein for the treatment, prevention and/or delay of progression of central nervous system (CNS) conditions, wherein said CNS condition is selected from cognitive deficits in neurofibromatosis type I.

In a particular embodiment, the invention provides a GABA A α5 negative allosteric modulator as described herein for the treatment, prevention and/or delay of progression of central nervous system (CNS) conditions, wherein said CNS condition is selected from cognitive deficits after stroke In a particular embodiment, the invention provides a GABA A α5 negative allosteric modulator as described herein for the treatment, prevention and/or delay of progression of central nervous system (CNS) conditions, wherein said CNS condition is selected from intellectual disability. In a particular embodiment, the invention provides the use of a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from cognitive deficits in Down Syndrome, and wherein the GABA A α5 negative allosteric modulator is 3-Bromo-10-difluoromethyl-9H-imidazo[1,5-a][1,2,4]triazolo[1,5-d][1,4]benzodiazepine, or a pharmaceutically acceptable salt thereof.

In a particular embodiment, the invention provides the use of a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from cognitive deficits in Down Syndrome, and wherein the GABA A α5 negative allosteric modulator is (1,1-Dioxo-1,6-thiomorpholin-4-yl)-{6-[3-(4-fluoro-phenyl)-5-methyl-isoxazol-4-ylmethoxy]-pyridin-3-yl}-methanone; or a pharmaceutically acceptable salt thereof.

In a particular embodiment, the invention provides a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from cognitive deficits in Down Syndrome, and wherein the GABA A α5 negative allosteric modulator is 3-Bromo-10-difluoromethyl-9H-imidazo[1,5-a][1,2,4]triazolo[1,5-d][1,4]benzodiazepine, or a pharmaceutically acceptable salt thereof.

In a particular embodiment, the invention provides the a GABA A α5 negative allosteric modulator for the treatment, prevention and/or delay of progression of central nervous system (CNS) conditions caused by neurodevelopmental defects which result in excessive GABAergic inhibition in the cortex and hippocampus, wherein said CNS condition is selected from cognitive deficits in Down Syndrome, and wherein the GABA A α5 negative allosteric modulator is (1,1-Dioxo-1,6-thiomorpholin-4-yl)-{6-[3-(4-fluoro-phenyl)-5-methyl-isoxazol-4-ylmethoxy]-pyridin-3-yl}-methanone; or a pharmaceutically acceptable salt thereof.

In another embodiment, the invention provides the use of a GABA A α5 negative allosteric modulator selected from a compound of formula (I) or a compound of formula (II)

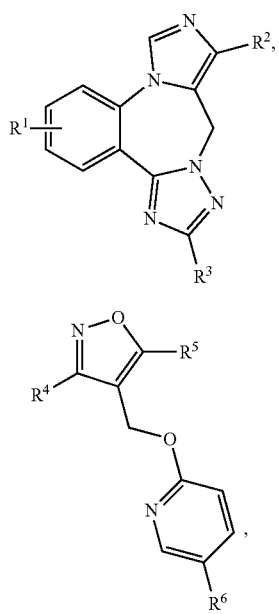

wherein
R¹ is hydrogen, halo, alkyl, haloalkyl, or cyano;
R² is hydrogen, halo, alkyl, haloalkyl, or cyano;
R³ is hydrogen, alkyl, or heterocycloalkylalkyl, wherein heterocycloalkylalkyl is optionally substituted with one or more hydroxy, oxo, alkyl, alkoxy, haloalkyl, hydroxyalkyl, halo, or cyano;
R⁴ is aryl or heteroaryl, each optionally substituted by one, two or three halo;
R⁵ is hydrogen, alkyl, haloalkyl or hydroxyalkyl;
R⁶ is —C(O)—NR⁷R⁸
R⁷ is hydrogen;
R⁸ is alkyl;
or R⁷ and R⁸ together with the nitrogen to which they are bound form a heterocycloalkyl, or a heteroaryl, each optionally substituted with one or more hydroxy, oxo, alkyl, alkoxy, haloalkyl, hydroxyalkyl, halo, or cyano;
or a pharmaceutically acceptable salt thereof;
for the treatment, prevention and/or delay of progression of central nervous system (CNS) conditions related to excessive GABAergic inhibition in the cortex and hippocampus.

In a particular embodiment, the invention provides the use of a GABA A α5 negative allosteric modulator as described above for the treatment, prevention and/or delay of progression of central nervous system (CNS) conditions related to excessive GABAergic inhibition in the cortex and hippocampus, wherein the excessive GABAergic inhibition in the cortex and hippocampus is caused by neurodevelopmental defects.

In a particular embodiment, the invention provides the use of a GABA A α5 negative allosteric modulator as described above for the treatment, prevention and/or delay of progression of central nervous system (CNS) conditions caused by neurodevelopmental defects which result in excessive GABAergic inhibition in the cortex and hippocampus.

In a particular embodiment, the invention provides the use of a GABA A α5 negative allosteric modulator as described above for the treatment, prevention and/or delay of progression of central nervous system (CNS) conditions related to excessive GABAergic inhibition in the cortex and hippocampus, particularly caused by neurodevelopmental defects, wherein said CNS condition is selected from cognitive deficits in Down Syndrome, in autism or in neurofibromatosis type I.

In a particular embodiment, the invention provides the use of a GABA A α5 negative allosteric modulator as described above for the treatment, prevention and/or delay of progression of central nervous system (CNS) conditions related to excessive GABAergic inhibition in the cortex and hippocampus, particularly caused by neurodevelopmental defects, wherein said CNS condition is cognitive deficits in Down Syndrome.

In a particular embodiment, the invention provides the use of a GABA A α5 negative allosteric modulator as described above for the treatment, prevention and/or delay of progression of central nervous system (CNS) conditions related to excessive GABAergic inhibition in the cortex and hippocampus, particularly caused by neurodevelopmental defects, wherein said CNS condition is cognitive deficits in autism.

In a particular embodiment, the invention provides the use of a GABA A α5 negative allosteric modulator as described above for the treatment, prevention and/or delay of progression of central nervous system (CNS) conditions related to excessive GABAergic inhibition in the cortex and hippocampus, particularly caused by neurodevelopmental defects, wherein said CNS condition is cognitive deficits in neurofibromatosis type I.

In a particular embodiment, the invention provides the use of a GABA A α5 negative allosteric modulator as described above for the treatment, prevention and/or delay of progression of central nervous system (CNS) conditions related to excessive GABAergic inhibition in the cortex and hippocampus, wherein said CNS condition is characterized by disabilities after stroke.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is binding to human GABA A α5β3γ2 receptor subtype with a binding selectivity of a factor of 10 or more as compared to binding affinities to human GABA A α1β2/3γ2, α2β2/3γ2 and α3β2/3γ2 receptor subtypes.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator exhibits a functional selectivity by acting as inverse agonist at human GABA A α5β3γ2 receptor subtype by reducing the effect of GABA by more than 30% and in addition affecting the effect of GABA at human GABA A α1β2/3γ2, α2β2/3γ2 and α3β2/3γ2 receptor subtypes by less than 15%.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is selected from a compound of formula (I), wherein $R^1$, $R^2$, and $R^3$ are as defined herein, or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is selected from a compound of formula (I), wherein $R^1$ is hydrogen, halo, haloalkyl, or cyano; $R^2$ is halo, or haloalkyl; $R^3$ is hydrogen, alkyl, or heterocycloalkylalkyl substituted with one oxo; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is selected from
3-Fluoro-10-fluoromethyl-9H-imidazo[1,5-a][1,2,4]triazolo[1,5-d][1,4]benzodiazepine;
3-Bromo-10-difluoromethyl-9H-imidazo[1,5-a][1,2,4]triazolo[1,5-d][1,4]benzodiazepine;
3-Cyano-10-difluoromethyl-9H-imidazo[1,5-a][1,2,4]triazolo[1,5-d][1,4]benzodiazepine;
10-Difluoromethyl-9H-imidazo[1,5-a][1,2,4]triazolo[1,5-d][1,4]benzodiazepine;
3-Chloro-10-fluoromethyl-6-methyl-9H-imidazo[1,5-a][1,2,4]triazolo[1,5-d][1,4]benzodiazepine;
10-Chloro-9H-imidazo[1,5-a][1,2,4]triazolo[1,5-d][1,4]benzodiazepine;
3,10-Dichloro-9H-imidazo[1,5-a][1,2,4]triazolo[1,5-d][1,4]benzodiazepine;
10-Chloro-3-cyano-6-methyl-9H-imidazo[1,5-a][1,2,4]triazolo[1,5-d][1,4]benzodiazepine;
10-Chloro-3-difluoromethyl-9H-imidazo[1,5-a][1,2,4]triazolo[1,5-d][1,4]benzodiazepine;
3-Bromo-10-chloro-6-methyl-9H-imidazo[1,5-a][1,2,4]triazolo[1,5-d][1,4]benzodiazepine;
10-Bromo-3-fluoro-9H-imidazo[1,5-a][1,2,4]triazolo[1,5-d][1,4]benzodiazepine;
3-Bromo-10-methyl-6-(2-oxo-pyrrolidin-1-ylmethyl)-9H-imidazo[1,5-a][1,2,4]triazolo[1,5-d][1,4]benzodiazepine;
or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is selected from a compound of formula (II) wherein $R^4$, $R^5$, and $R^6$ are as defined herein, or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is selected from a compound of formula (II) wherein $R^4$ is aryl or heteroaryl, each optionally substituted by one halo; $R^5$ is alkyl; $R^6$ is C(O)—$NR^7R^8$; $R^7$ is hydrogen and $R^8$ is alkyl; or $R^7$ and $R^8$ together with the nitrogen to which they are bound form a heterocycloalkyl optionally substituted with one or two oxo, or form a heteroaryl; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is selected from:
N-Isopropyl-6-(5-methyl-3-phenyl-isoxazol-4-ylmethoxy)-nicotinamide;
(5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone;
[6-(5-Methyl-3-phenyl-isoxazol-4-ylmethoxy)-pyridin-3-yl]-(2-oxa-6-aza-spiro[3.3]hept-6-yl)-methanone;
(1,1-Dioxo-1,6-thiomorpholin-4-yl)-{6-[3-(4-fluoro-phenyl)-5-methyl-isoxazol-4-ylmethoxy]-pyridin-3-yl}-methanone;
{6-[3-(4-Chloro-phenyl)-5-methyl-isoxazol-4-ylmethoxy]-pyridin-3-yl}-morpholin-4-yl-methanone;
[6-(5-Methyl-3-pyridin-2-yl-isoxazol-4-ylmethoxy)-pyridin-3-yl]-morpholin-4-yl-methanone;
6-[3-(5-Fluoro-pyridin-2-yl)-5-methyl-isoxazol-4-ylmethoxy]-isopropyl-nicotinamide;
(1,1-Dioxo-1,6-thiomorpholin-4-yl)-{6-[3-(5-fluoro-pyridin-2-yl)-5-methyl-isoxazol-4-ylmethoxy]-pyridin-3-yl}-methanone;
{6-[3-(5-Chloro-pyridin-2-yl)-5-methyl-isoxazol-4-ylmethoxy]-pyridin-3-yl}-thiomorpholin-4-yl-methanone;
or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is N-Isopropyl-6-(5-methyl-3-phenyl-isoxazol-4-ylmethoxy)-nicotinamide; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is (5,6-Dihydro-8H-[1,2,4]triazolo[4,3-a]pyrazin-7-yl)-[6-(5-methyl-3- phenyl-isoxazol-4-ylmethoxy)-pyridin-3-yl]-methanone; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is [6-(5-Methyl-3-phenyl-isoxazol-4-ylmethoxy)-pyridin-3-yl]-(2-oxa-6-aza-spiro[3.3]hept-6-yl)-methanone; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is (1,1-Dioxo-1,6-thiomorpholin-4-yl)-{6-[3-(4-fluoro-phenyl)-5-methyl-isoxazol-4-ylmethoxy]-pyridin-3-yl}-methanone; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is {6-[3-(4-Chloro-phenyl)-5-methyl-isoxazol-4-ylmethoxy]-pyridin-3-yl}-morpholin-4-yl-methanone; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is [6-(5-Methyl-3-pyridin-2-yl-isoxazol-4-ylmethoxy)-pyridin-3-yl]-morpholin-4-yl-methanone; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is 6-[3-(5-Fluoro-pyridin-2-yl)-5-methyl-isoxazol-4-ylmethoxy]-isopropyl-nicotinamide; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is (1,1-Dioxo-1,6-thiomorpholin-4-yl)-{6-[3-(5-fluoro-pyridin-2-yl)-5-methyl-isoxazol-4-ylmethoxy]-pyridin-3-yl}-methanone; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is {6-[3-(5-Chloro-pyridin-2-yl)-5-methyl-isoxazol-4-ylmethoxy]-pyridin-3-yl}-thiomorpholin-4-yl-methanone; or a pharmaceutically acceptable salt thereof.

In a particular embodiment, the invention provides the use of a GABA A α5 negative allosteric modulator for the treatment, prevention and/or delay of progression of central nervous system (CNS) conditions as described herein, wherein said GABA A α5 negative allosteric modulator is used separately, sequentially or simultaneously in combination with a second active pharmaceutical compound.

In a particular embodiment, the invention provides a method for the treatment, prevention and/or delay of progression of cognitive deficits in Down Syndrome, in autism, in neurofibromatosis type I, or for recovery after stroke in a subject in need of such treatment, which comprises administering to said subject a therapeutically effective amount of a GABA A α5 negative allosteric modulator as described herein in a pharmaceutically acceptable form.

In a particular embodiment, the invention provides a pharmaceutical composition comprising a GABA A α5 negative allosteric modulator as described herein in a pharmaceutically acceptable form for the treatment, prevention and/or delay of progression of cognitive deficits in Down Syndrome, in autism, in neurofibromatosis type I, or for recovery after stroke.

In a particular embodiment, the invention provides a GABA A α5 negative allosteric modulator as described herein for the treatment, prevention and/or delay of progression of cognitive deficits in Down Syndrome, in autism, in neurofibromatosis type I, or for recovery after stroke.

In a particular embodiment, the invention provides a GABA A α5 negative allosteric modulator as described herein for the preparation of medicaments for the treatment, prevention and/or delay of progression of cognitive deficits in Down Syndrome, in autism, in neurofibromatosis type I, or for recovery after stroke.

In a particular embodiment, the invention provides the use of a GABA A α5 negative allosteric modulator as described herein for the preparation of medicaments for the treatment, prevention and/or delay of progression of cognitive deficits in Down Syndrome, in autism, in neurofibromatosis type I, or for recovery after stroke.

In another embodiment, the invention provides a GABA A α5 negative allosteric modulator selected from a compound of formula (I) or a compound of formula (II)

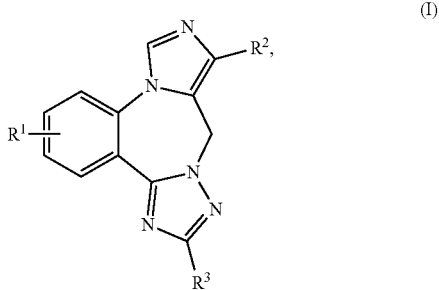

(I)

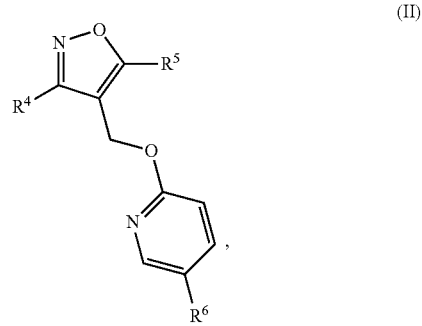

(II)

wherein
$R^1$ is hydrogen, halo, alkyl, haloalkyl, or cyano;
$R^2$ is hydrogen, halo, alkyl, haloalkyl, or cyano;
$R^3$ is hydrogen, alkyl, or heterocycloalkylalkyl, wherein heterocycloalkylalkyl is optionally substituted with one or more hydroxy, oxo, alkyl, alkoxy, haloalkyl, hydroxyalkyl, halo, or cyano;

R⁴ is aryl or heteroaryl, each optionally substituted by one, two or three halo;
R⁵ is hydrogen, alkyl, haloalkyl or hydroxyalkyl;
R⁶ is —C(O)—NR⁷R⁸
R⁷ is hydrogen;
R⁸ is alkyl;
or R⁷ and R⁸ together with the nitrogen to which they are bound form a heterocycloalkyl, or a heteroaryl, each optionally substituted with one or more hydroxy, oxo, alkyl, alkoxy, haloalkyl, hydroxyalkyl, halo, or cyano;
or a pharmaceutically acceptable salt thereof;
for the treatment, prevention and/or delay of progression of central nervous system (CNS) conditions related to excessive GABAergic inhibition in the cortex and hippocampus In a particular embodiment, the invention provides a GABA A α5 negative allosteric modulator as described herein for the treatment, prevention and/or delay of progression of central nervous system (CNS) conditions related to excessive GABAergic inhibition in the cortex and hippocampus, which is caused by neurodevelopmental defects.

In a particular embodiment, the invention provides a GABA A α5 negative allosteric modulator as described herein for the treatment, prevention and/or delay of progression of central nervous system (CNS) conditions caused by neurodevelopmental defects which result in excessive GABAergic inhibition in the cortex and hippocampus.

In a particular embodiment, the invention provides a GABA A α5 negative allosteric modulator as described herein for the treatment, prevention and/or delay of progression of central nervous system (CNS) conditions related to excessive GABAergic inhibition in the cortex and hippocampus, particularly caused by neurodevelopmental defects, wherein said CNS condition is selected from cognitive deficits in Down Syndrome, in autism or in neurofibromatosis type I.

In a particular embodiment, the invention provides a GABA A α5 negative allosteric modulator as described herein for the treatment, prevention and/or delay of progression of central nervous system (CNS) conditions related to excessive GABAergic inhibition in the cortex and hippocampus, particularly caused by neurodevelopmental defects, wherein said CNS condition is cognitive deficits in Down Syndrome.

In a particular embodiment, the invention provides a GABA A α5 negative allosteric modulator as described herein for the treatment, prevention and/or delay of progression of central nervous system (CNS) conditions related to excessive GABAergic inhibition in the cortex and hippocampus, particularly caused by neurodevelopmental defects, wherein said CNS condition is cognitive deficits in autism.

In a particular embodiment, the invention provides a GABA A α5 negative allosteric modulator as described herein for the treatment, prevention and/or delay of progression of central nervous system (CNS) conditions related to excessive GABAergic inhibition in the cortex and hippocampus, particularly caused by neurodevelopmental defects, wherein said CNS condition is cognitive deficits in neurofibromatosis type I.

In a particular embodiment, the invention provides a GABA A α5 negative allosteric modulator as described herein for the treatment, prevention and/or delay of progression of central nervous system (CNS) conditions related to excessive GABAergic inhibition in the cortex and hippocampus, wherein said CNS condition is characterized by disabilities after stroke.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is binding to human GABA A α5β3γ2 receptor subtype with a binding selectivity of a factor of 10 or more as compared to binding affinities to human GABA A α1β2/3γ2, α2β2/3γ2 and α3β2/3γ2 receptor subtypes.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator exhibits a functional selectivity by acting as inverse agonist at human GABA A α5β3γ2 receptor subtype by reducing the effect of GABA by more than 30% and in addition affecting the effect of GABA at human GABA A α1β2/3γ2, α2β3γ2 and α3β3γ2 receptor subtypes by less than 15%.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is selected from a compound of formula (I), wherein R¹, R², and R³ are as defined herein, or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is selected from a compound of formula (I), wherein R¹ is hydrogen, halo, haloalkyl, or cyano; R² is halo, or haloalkyl; R³ is hydrogen, alkyl, or heterocycloalkylalkyl substituted with one oxo; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is selected from
3-Fluoro-10-fluoromethyl-9H-imidazo[1,5-a][1,2,4]triazolo[1,5-d][1,4]benzodiazepine;
3-Bromo-10-difluoromethyl-9H-imidazo[1,5-a][1,2,4]triazolo[1,5-d][1,4]benzodiazepine;
3-Cyano-10-difluoromethyl-9H-imidazo[1,5-a][1,2,4]triazolo[1,5-d][1,4]benzodiazepine;
10-Difluoromethyl-9H-imidazo[1,5-a][1,2,4]triazolo[1,5-d][1,4]benzodiazepine;
3-Chloro-10-fluoromethyl-6-methyl-9H-imidazo[1,5-a][1,2,4]triazolo[1,5-d][1,4]benzodiazepine;
10-Chloro-9H-imidazo[1,5-a][1,2,4]triazolo[1,5-d][1,4]benzodiazepine;
3,10-Dichloro-9H-imidazo[1,5-a][1,2,4]triazolo[1,5-d][1,4]benzodiazepine;
10-Chloro-3-cyano-6-methyl-9H-imidazo[1,5-a][1,2,4]triazolo[1,5-d][1,4]benzodiazepine;
10-Chloro-3-difluoromethyl-9H-imidazo[1,5-a][1,2,4]triazolo[1,5-d][1,4]benzodiazepine;
3-Bromo-10-chloro-6-methyl-9H-imidazo[1,5-a][1,2,4]triazolo[1,5-d][1,4]benzodiazepine;
10-Bromo-3-fluoro-9H-imidazo[1,5-a][1,2,4]triazolo[1,5-d][1,4]benzodiazepine;
3-Bromo-10-methyl-6-(2-oxo-pyrrolidin-1-ylmethyl)-9H-imidazo[1,5-a][1,2,4]triazolo[1,5-d][1,4]benzodiazepine;
or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is 3-Bromo-10-difluoromethyl-9H-imidazo[1,5-a][1,2,4]triazolo[1,5-d][1,4]benzodiazepine or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is not 3-Bromo-10-difluoromethyl-9H-imidazo[1,5-a][1,2,4]triazolo[1,5-d][1,4]benzodiazepine or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is selected from a compound of formula (II) wherein $R^4$, $R^5$, and $R^6$ are as defined herein, or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is selected from a compound of formula (II) wherein $R^4$ is aryl or heteroaryl, each optionally substituted by one halo; $R^5$ is alkyl; $R^6$ is C(O)—$NR^7R^8$; $R^7$ is hydrogen and $R^8$ is alkyl; or $R^7$ and $R^8$ together with the nitrogen to which they are bound form a heterocycloalkyl optionally substituted with one or two oxo, or form a heteroaryl; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is selected from:
N-Isopropyl-6-(5-methyl-3-phenyl-isoxazol-4-ylmethoxy)-nicotinamide;
(5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone;
[6-(5-Methyl-3-phenyl-isoxazol-4-ylmethoxy)-pyridin-3-yl]-(2-oxa-6-aza-spiro[3.3]hept-6-yl)-methanone;
(1,1-Dioxo-1,6-thiomorpholin-4-yl)-{6-[3-(4-fluoro-phenyl)-5-methyl-isoxazol-4-ylmethoxy]-pyridin-3-yl}-methanone;
{6-[3-(4-Chloro-phenyl)-5-methyl-isoxazol-4-ylmethoxy]-pyridin-3-yl}-morpholin-4-yl-methanone;
[6-(5-Methyl-3-pyridin-2-yl-isoxazol-4-ylmethoxy)-pyridin-3-yl]-morpholin-4-yl-methanone;
6-[3-(5-Fluoro-pyridin-2-yl)-5-methyl-isoxazol-4-ylmethoxy]-isopropyl-nicotinamide;
(1,1-Dioxo-1,6-thiomorpholin-4-yl)-{6-[3-(5-fluoro-pyridin-2-yl)-5-methyl-isoxazol-4-ylmethoxy]-pyridin-3-yl}-methanone;
{6-[3-(5-Chloro-pyridin-2-yl)-5-methyl-isoxazol-4-ylmethoxy]-pyridin-3-yl}-thiomorpholin-4-yl-methanone; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator N-Isopropyl-6-(5-methyl-3-phenyl-isoxazol-4-ylmethoxy)-nicotinamide; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is (5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is [6-(5-Methyl-3-phenyl-isoxazol-4-ylmethoxy)-pyridin-3-yl]-(2-oxa-6-aza-spiro[3.3]hept-6-yl)-methanone; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is (1,1-Dioxo-1,6-thiomorpholin-4-yl)-{6-[3-(4-fluoro-phenyl)-5-methyl-isoxazol-4-ylmethoxy]-pyridin-3-yl}-methanone or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is {6-[3-(4-Chloro-phenyl)-5-methyl-isoxazol-4-ylmethoxy]-pyridin-3-yl}-morpholin-4-yl-methanone; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is [6-(5-Methyl-3-pyridin-2-yl-isoxazol-4-ylmethoxy)-pyridin-3-yl]-morpholin-4-yl-methanone; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is 6-[3-(5-Fluoro-pyridin-2-yl)-5-methyl-isoxazol-4-ylmethoxy]-isopropyl-nicotinamide; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is (1,1-Dioxo-1,6-thiomorpholin-4-yl)-{6-[3-(5-fluoro-pyridin-2-yl)-5-methyl-isoxazol-4-ylmethoxy]-pyridin-3-yl}-methanone; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is {6-[3-(5-Chloro-pyridin-2-yl)-5-methyl-isoxazol-4-ylmethoxy]-pyridin-3-yl}-thiomorpholin-4-yl-methanone; or a pharmaceutically acceptable salt thereof.

In a particular embodiment, the invention provides a GABA A α5 negative allosteric modulator as described herein for the treatment, prevention and/or delay of progression of central nervous system (CNS) conditions as described herein, wherein said GABA A α5 negative allosteric modulator is used separately, sequentially or simultaneously in combination with a second active pharmaceutical compound.

EXAMPLES

Materials and Methods
a. Animals

Table 1 shows the number of male animals that were used in this study. Ten control and ten Ts65Dn mice of 6 months of age at the beginning of the treatment received 8581; 16 control and 15 Ts65Dn mice of 5-6 months of age at the beginning of the treatment received R1, the other two groups of control (n=13) and Ts65Dn (n=13) mice received vehicle.
b. Active Pharmaceutical Compounds Active pharmaceutical compounds used in present invention were prepared as described previously in WO 2006/045429, WO 2006/045430, WO 2007/042421 and WO 2009/071476:
Compound 8580
  3-Fluoro-10-fluoromethyl-9H-imidazo[1,5-a][1,2,4]triazolo[1,5-d][1,4]benzodiazepine was prepared as described in WO 2006/045430 on page 17 in Example 3.
Compound 8581
  3-Bromo-10-difluoromethyl-9H-imidazo[1,5-a][1,2,4]triazolo[1,5-d][1,4]benzodiazepine was prepared as described in WO 2006/045430 on page 21 in Example 7.
Compound 8582
  3-Cyano-10-difluoromethyl-9H-imidazo[1,5-a][1,2,4]triazolo[1,5-d][1,4]benzodiazepine was prepared as described in WO 2006/045430 on page 23 in Example 13.
Compound 8583
  10-Difluoromethyl-9H-imidazo[1,5-a][1,2,4]triazolo[1,5-d][1,4]benzodiazepine was prepared as described in WO 2006/045430 on page 26 in Example 16.
Compound 8584
  3-Chloro-10-fluoromethyl-6-methyl-9H-imidazo[1,5-a][1,2,4]triazolo[1,5-d][1,4]benzodiazepine was prepared as described in WO 2006/045430 on page 28 in Example 20.
Compound 8585
  10-Chloro-9H-imidazo[1,5-a][1,2,4]triazolo[1,5-d][1,4]benzodiazepine was prepared as described in WO 2006/045429 on page 15 in Example 1.
Compound 8586
  3,10-Dichloro-9H-imidazo[1,5-a][1,2,4]triazolo[1,5-d][1,4]benzodiazepine was prepared as described in WO 2006/045429 on page 23 in Example 20.
Compound 8587
  10-Chloro-3-cyano-6-methyl-9H-imidazo[1,5-a][1,2,4]triazolo[1,5-d][1,4]benzodiazepine was prepared as described in WO 2006/045429 on page 37 in Example 47.
Compound 8588
  10-Chloro-3-difluoromethyl-9H-imidazo[1,5-a][1,2,4]triazolo[1,5-d][1,4]benzodiazepine was prepared as described in WO 2006/045429 on page 29 in Example 32.
Compound 8589
  3-Bromo-10-chloro-6-methyl-9H-imidazo[1,5-a][1,2,4]triazolo[1,5-d][1,4]benzodiazepine was prepared as described in WO 2006/045429 on page 33 in Example 38.
Compound 8590
  10-Bromo-3-fluoro-9H-imidazo[1,5-a][1,2,4]triazolo[1,5-d][1,4]benzodiazepine was prepared as described in WO 2006/045429 on page 37 in Example 47.
Compound 8591
  3-Bromo-10-methyl-6-(2-oxo-pyrrolidin-1-ylmethyl)-9H-imidazo[1,5-a][1,2,4]triazolo[1,5-d][1,4]benzodiazepine was prepared as described in WO 2007/042421 on page 67 in Example 101.
Compound O1
  N-Isopropyl-6-(5-methyl-3-phenyl-isoxazol-4-ylmethoxy)-nicotinamide was prepared as described in WO 2009/071476 on page 50 in Example 26.
Compound P1
  (5,6-Dihydro-8H-[1,2,4]triazolo[4,3-a]pyrazin-7-yl)-[6-(5-methyl-3-phenyl-isoxazol-4-ylmethoxy)-pyridin-3-yl]-methanone was prepared as described in WO 2009/071476 on page 62 in Example 75.
Compound Q1
  [6-(5-Methyl-3-phenyl-isoxazol-4-ylmethoxy)-pyridin-3-yl]-(2-oxa-6-aza-spiro[3.3]hept-6-yl)-methanone was prepared as described in WO 2009/071476 on page 64 in Example 81.
Compound R1
  (1,1-Dioxo-1,6-thiomorpholin-4-yl)-{6-[3-(4-fluoro-phenyl)-5-methyl-isoxazol-4-ylmethoxy]-pyridin-3-yl}-methanone was prepared as described in WO 2009/071476 on page 75 in Example 112.
Compound S1
  {6-[3-(4-Chloro-phenyl)-5-methyl-isoxazol-4-ylmethoxy]-pyridin-3-yl}-morpholin-4-yl-methanone was prepared as described in WO 2009/071476 on page 78 in Example 123.
Compound T1
  [6-(5-Methyl-3-pyridin-2-yl-isoxazol-4-ylmethoxy)-pyridin-3-yl]-morpholin-4-yl-methanone was prepared as described in WO 2009/071476 on page 123 in Example 274.
Compound U1
  6-[3-(5-Fluoro-pyridin-2-yl)-5-methyl-isoxazol-4-ylmethoxy]-isopropyl-nicotinamide was prepared as described in WO 2009/071476 on page 127 in Example 289.
Compound V1
  (1,1-Dioxo-1λ,6-thiomorpholin-4-yl)-{6-[3-(5-fluoro-pyridin-2-yl)-5-methyl-isoxazol-4-ylmethoxy]-pyridin-3-yl}-methanone was prepared as described in WO 2009/071476 on page 127 in Example 293.
Compound W1
  {6-[3-(5-Chloro-pyridin-2-yl)-5-methyl-isoxazol-4-ylmethoxy]-pyridin-3-yl}-thiomorpholin-4-yl-methanone was prepared as described in WO 2009/071476 on page 132 in Example 310.

The binding affinities of the above active pharmaceutical compounds at the GABA A receptor subtypes have been measured by competition for [$^3$H]flumazenil (85 Ci/mmol; Roche) binding to HEK293 cells expressing rat (stably transfected) or human (transiently transfected) receptors of composition α1β2/3γ2, α2β3γ2, α3β3γ2, and α5β3γ2. As can be seen from Table 2a, active pharmaceutical compounds used in this invention exhibit high affinity at the α5β3γ2 receptor subtype and good selectivity over α1β2/3γ2, α2β3γ2 and α3β3γ2 receptor subtypes.

As can be seen from Table 2b, the active pharmaceutical compounds used in present invention also demonstrate a substantial functional selectivity. Subtype-selective effects were determined on cloned receptors expressed in *Xenopus* oocytes. Human recombinant GABA A receptors were expressed in *Xenopus laevis* oocytes. Current responses were evoked in two-microelectrode voltage-clamp condition by applying an EC10 of GABA before and during the co-application of the test compound. Response amplitudes in the presence of the test compound are expressed as percentage of the amplitudes before drug addition.

c. Pharmaceutical Compositions

For mice studies, active pharmaceutical compounds of present invention were formulated in chocolate-milk (Puleva, Barcelona, Spain). Active pharmaceutical compounds of present invention or vehicle were administered p.o. at a dose of 20 mg/kg for six weeks. Their administration was prolonged during the 30 days of the behavioral assessment.

For human use pharmaceutical compositions or medicaments can be prepared comprising active pharmaceutical compounds as described above and a therapeutically inert carrier, diluent or excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The active pharmaceutical compounds used in the invention can be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The active pharmaceutical compounds used in the invention can be administered in any convenient administrative form, e.g., tablets, powders, capsules, solutions, dispersions, suspensions, syrups, sprays, suppositories, gels, emulsions, patches, etc. Such compositions can comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical pharmaceutical composition is prepared by mixing an active pharmaceutical compounds used in the invention t and a carrier or excipient. Suitable carriers and excipients are well known to those skilled in the art and are described in detail in, e.g., Ansel H. C. et al., Ansel's Pharmaceutical Dosage Forms and Drug Delivery Systems (2004) Lippincott, Williams & Wilkins, Philadelphia; Gennaro A. R. et al., Remington: The Science and Practice of Pharmacy (2000) Lippincott, Williams & Wilkins, Philadelphia; and Rowe R. C, Handbook of Pharmaceutical Excipients (2005) Pharmaceutical Press, Chicago. The pharmaceutical compositions can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which active pharmaceutical compounds used in the invention can be administered can vary within wide limits and will, of course, be fitted to the individual requirements in each particular case. In general, in the case of oral administration a daily dosage of about 0.1 to 1500 mg, more particular 1 to 1000 mg, most particular 5 to 500 mg per person of an active pharmaceutical compounds used in the invention should be appropriate, although the above upper limit can also be exceeded when necessary.

An example of a suitable oral dosage form is a tablet comprising about 100 mg to 500 mg of an active pharmaceutical compounds used in the invention compounded with about 90 to 30 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol composition can be prepared by dissolving an active pharmaceutical compounds used in the invention, for example 10 to 100 mg, in a suitable buffer solution, e.g. a phosphate buffer, adding a tonicifier, e.g. a salt such as sodium chloride, if desired. The solution can be filtered, e.g., using a 0.2 µm filter, to remove impurities and contaminants.

d. Statistical Analysis

The data were analyzed using two-way ('genotype'×'treatment') ANOVAs. The Morris water maze data were analyzed using a two-way ANOVA with repeated measures ('session'× 'genotype'×'treatment'). The means of each experimental group were compared post-hoc by Student's t-test if two groups were compared or Bonferroni tests if more than two groups were compared. All the analyses were done using SPSS for Windows version 17.0 (SPSS AG, Zurich, Switzerland).

EXAMPLE 1

Sensorimotor Tests

A battery of sensorimotor tests was performed following the procedure described by Rueda N et al. [*Neurosci Lett* (2008) 433(1):22-27]. In the visual placing reflex test, cerebellar and vestibular functions were evaluated. In 3 consecutive trials, mice were gently lowered by the tail towards a flat surface from a height of 15 cm. The response of forepaw extension was scored on a 0-4 scale [4: animal extends the forepaws when placed at the highest height; 3: forepaws extended before touching the surface with vibrissae; 2: forepaws extended after vibrissae touched the surface; 1: forepaws extended after the nose touched the surface; 0: no extension].

To evaluate auditory sensitivity, the startle response to a sudden auditory stimulus was measured. Mice were placed facing the wall of an unfamiliar cage and the auditory stimulus was generated by clapping together two stainless steel forceps (7 cm long). A score (0-3 points) was assigned based on the magnitude of the response: jumping more than 1 cm (3 points); jumping less than 1 cm (2 points); retracting of the ears (Preyer reflex, 1 point); or no response (0 points).

The vibrissa placing reflex was analyzed by noting the reflective reaction to touching the vibrissae with a cotton stick. In three consecutive trials, a score of 1 was assigned to animals that touched the stimulated vibrissae with an ipsilateral paw, and 0 if there was no response. Grip strength was assessed by quantifying the resistance to being separated from a lid of aluminum bars (2 mm), when dragged by the tail (0: no resistance, total loss of grip strength; 1: slight; 2: moderate; 3: active; 4: extremely active resistance, normal grip strength).

In order to evaluate equilibrium, four 20-s trials of balance were performed on an elevated (40 cm high), horizontal (50 cm long) rod. Trials 1 and 2 were performed on a flat wooden rod (9 mm wide); trials 3 and 4 were performed on a cylindrical aluminum rod (1 cm diameter). In each trial, the animals were placed in a marked central zone (10 cm) on the elevated rod. A score of 0 was given if the animal fell within 20 s, 1 if it stayed within the central zone for >20 s, 2 if it left the central zone, and 3 if it reached one of the ends of the bar.

Prehensile reflex (three 5-s trials) was measured as the ability of the animal to remain suspended by the forepaws by grasping an elevated horizontal wire (2 mm in diameter). The maximum possible score of 3 was achieved when the animal remained suspended by the forepaws in all three trials (one point per trial). Traction capacity was scored at the same time by assessing the number of hind limbs that the animal raised to reach the wire (0: none; 1: one limb; 2: two limbs).

Table 3 shows the score of 8581-, R1- and vehicle-treated Ts65Dn and control mice in the different sensorimotor tests. 8581 or R1 treatment did not modify any of the sensorimotor abilities tested in Ts65Dn or control mice (vision, audition, strength, equilibrium prehensile reflex, traction capacity or motor coordination in the coat hanging test).

Example 2

Motor Coordination: Rotarod

Motor coordination was evaluated using a rotarod device (Ugo Basile; Comerio, Italy), which consists of a 37-cm-long, 3-cm diameter plastic rod that rotates at different speeds. In a single session, 4 trials with a maximum duration of 60 s each were performed. In the first three tests, the rod was rotated at constant speeds of 5, 25 and 50 rpm, respectively. The last trial consisted of an acceleration cycle, in which the rod rotated progressively faster, and the animal had to adapt to the growing demands of the test. The length of time that each animal stayed on the rotarod was recorded.

Figure 2:
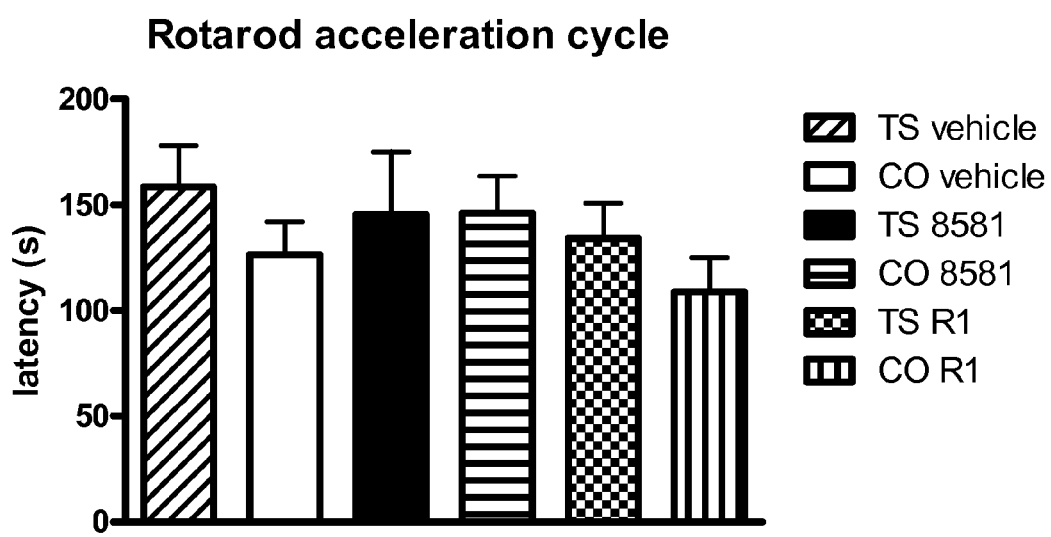
FIG. 2. Mean±S.E.M. of the latency of 8581-, R1- and vehicle-treated Ts65Dn and control mice to fall from the rotarod during the acceleration cycle.

As shown in FIGS. 1 and 2 motor coordination in the rotarod was not modified in mice of either genotype after 8581- or R1-treatment. Ts65Dn and control mice did not differ in the latency to fall from the rotarod at different constant speeds (ANOVA 'genotype': vel 2: $F(1,76)=0.63$, $p=0.42$; vel 3: $F(1,76)=1.54$, $p=0.21$) or during the acceleration cycle ($F(1,76)=1.87$, $p=0.17$).

Furthermore, no differences were found between 8581- or R1- and vehicle-treated Ts65Dn or control mice in the latency to fall at the different constant speeds (ANOVA 'treatment' vel 2: $F(1,76)=0.08$, $p=0.92$); vel 3: $F(1,76)=1.42$, $p=0.24$) or during the acceleration cycle ($F(1,76)=1.40$, $p=0.25$).

MANOVA revealed that there was no significant interaction of the factors 'genotype' and 'treatment' in any of the conditions tested in the rotarod (vel 2: $F(1,76)=0.31$, $p=0.72$; vel 3: $F(1,76)=0.48$, $p=0.61$; acceleration. $F(1,76)=0.43$, $p=0.64$).

Example 3

Spontaneous Activity: Actimetry

In this test the circadian variation of the animals' spontaneous locomotor activity during a complete light-dark cycle of 24 hours was evaluated. The apparatus is a device (Actisystem II, Panlab, Barcelona) that detects the changes produced in a magnetic field by the movement of the mice. It registers the movements of animals during a continuous 24 hour cycle (12 hours of light and 12 hours of darkness).

Figure 3:
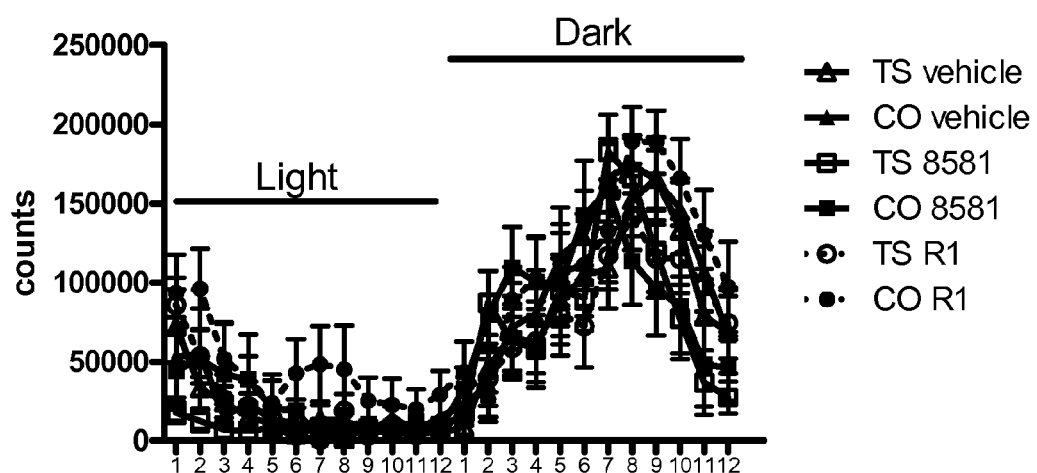
FIG. 3. Mean±S.E.M. of the spontaneous activity performed by Ts65Dn and control mice under vehicle R1 or 8581 treatment in their home-cage across a complete dark-light cycle of 24 hours.
Figure 4:
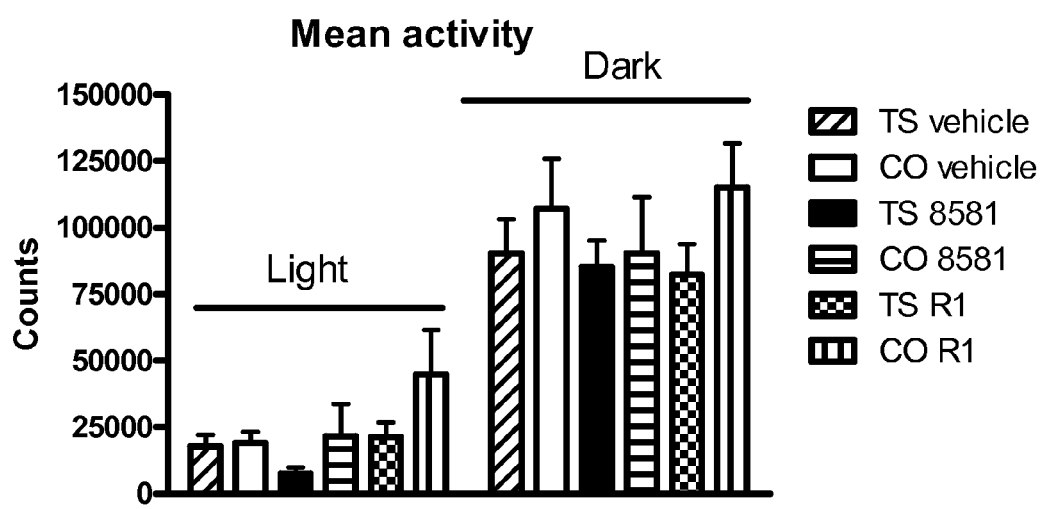
FIG. 4. Mean±S.E.M. of the mean activity performed by Ts65Dn and control mice under vehicle, R1 or 8581 treatment in the light and the dark phase of the cycle.

FIGS. 3 and 4 show that Ts65Dn and control mice (ANOVA 'genotype' dark: $F(1,76)=2.79$, $p=0.10$; light: $F(1,76)=2.24$, $p=0.14$) under vehicle, R1 or 8581 treatment (ANOVA 'treatment' dark: $F(1,76)=2.20$, $p=0.12$, light: $F(1,76)=0.27$, $p=0.76$; ANOVA 'genotype×treatment': dark: $F(1,76)=0.79$, $p=0.45$; light: $F(1,76)=0.39$, $p=0.67$) did not differ in the amount of spontaneous activity performed in their home cage during the dark or the light phase of the cycle.

Example 4

Open Field

Exploratory behavior and anxiety were assessed using a square-shaped open field (55 cm×55 cm, surrounded by a 25-cm-tall fence), divided into 25 equal squares. The animals were placed in the center of the field, and the number of vertical (rearing) activities and horizontal crossings (from square to square, subdivided into center vs. peripheral crossings) were scored in a single 5-min trial.

Figure 5:
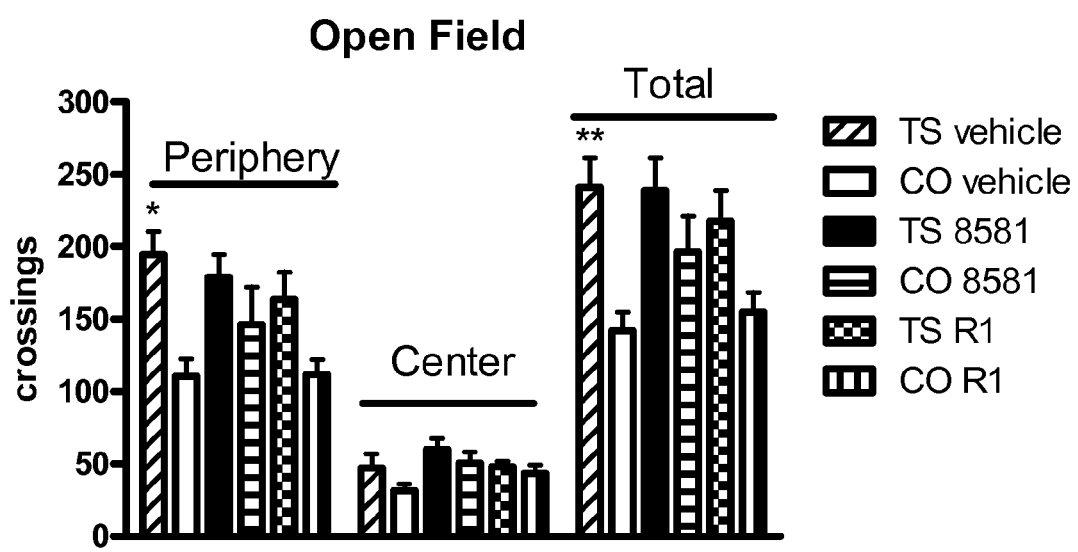
FIG. 5. Mean±S.E.M. of the number of crossings performed by R1-, 8581- and vehicle-treated Ts65Dn and control mice in the center and periphery of the open field. *: $p<0.05$; **: $p<0.01$ Bonferroni tests after significant ANOVA.
Figure 6:
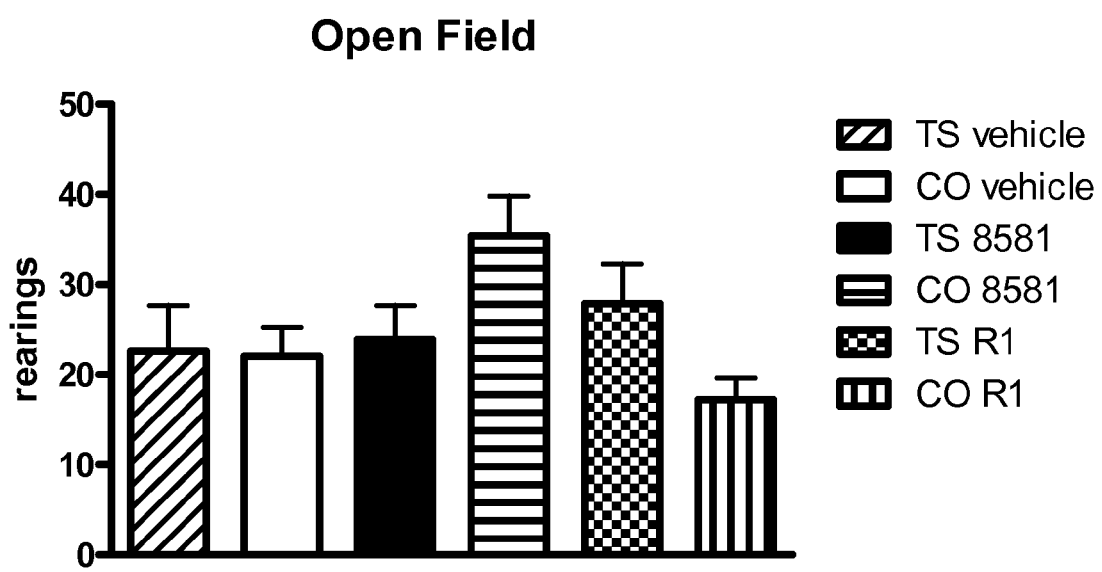
FIG. 6. Mean±S.E.M. of the number of rearings performed by R1- 8581- and vehicle-treated Ts65Dn and control mice in the open field.

In the Open Field test, no significant differences were found in the activity performed by mice of both genotypes in the center of the maze (ANOVA 'genotype': $F(1,76)=2.77$, $p=0.10$; FIG. 5) or in the number of rearings ($F(1,76)=0.01$, $p=0.90$; FIG. 6). However, vehicle-treated Ts65Dn mice were hyperactive when compared to control mice under the same treatment as shown by the increase in activity in the periphery (ANOVA 'genotype': $F(1,76)=15.86$, $p<0.001$; FIG. 5), and in total activity ($F(1,76)=17.39$, $p<0.001$; FIG. 6).

MANOVA revealed that R1- or 8581-treatment did not significantly affect horizontal (ANOVA 'treatment': periphery: $F(1,76)=1.08$, $p=0.34$; total number of crossings: $F(1,76)=1.27$, $p=0.28$) or vertical (rearings $F(1,76)=1.75$, $p=0.18$) activity in mice of either genotype. The fact that chronic administration of these two compounds did not affect activity in the center of the maze (ANOVA 'treatment': center: $F(1,76)=2.42$, $p=0.096$) suggests that these compounds did not produce an anxiogenic effect in mice or either genotypes. No significant interaction was found between 'genotype' and 'treatment' in horizontal activity (center $F(1,44)=0.64$, $p=0.71$; periphery: $F(1,76)=1.06$, $p=0.35$; total: $F(1,76)=1.00$, $p=0.37$) but ANOVA revealed a significant effect of these two factors on the number of rearings ($F(1,76)=3.36$, $p=0.04$).

Example 5

Exploratory Activity: Hole Board

The hole board is a wooden box (32×32×30 cm) with four holes. The floor is divided into nine 10 cm squares. In a single 5 minute trial the number of explorations, the time spent exploring each hole, and overall activity in the apparatus were measured. A repetition index was also calculated (exploration of holes previously explored) as a function of the number of ABA alternations.

Table 4 shows the scores of R1-, 8581- and vehicle-treated Ts65Dn and control mice in the Hole Board test. Ts65Dn mice under all treatments performed a larger number of crossings than control mice. 8581 and R1 treatment reduced this hyperactivity shown by Ts65Dn mice. Ts65Dn mice also showed an increase in the number of explorations performed under all treatment conditions. No differences were found in vertical activity in this maze among Ts65Dn and control mice under the different treatments. No significant differences were found between mice of both genotypes and treatments in the time they spent exploring the holes. Ts65Dn mice showed altered attention since they repeated a larger number of times the exploration of recently explored holes (ABA index). After 8581 (but not after R1) treatment, Ts65Dn mice ABA index was normalized.

Example 6

Spatial Learning: Morris Water Maze

Figure 7:
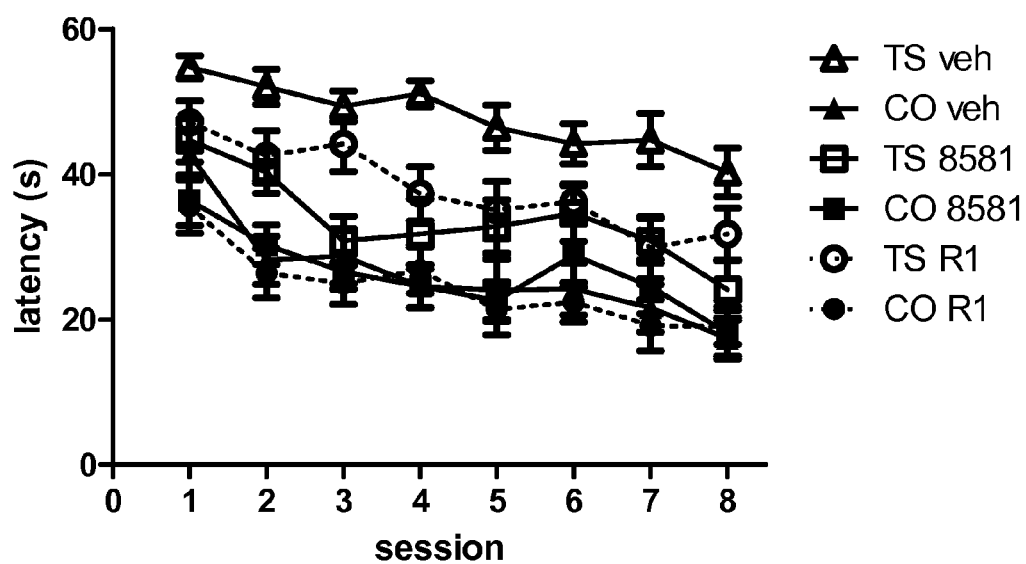
FIG. 7. Mean±S.E.M. of the latency to reach the platform during the eight acquisition sessions in the MWM.

To evaluate spatial learning the Morris Water Maze was used. The apparatus was a circular tank of 110 cm in diameter, full of water (22-24° C.) made opaque by the addition of powdered milk. Inside the tank, a platform was hidden 1 cm below the water level. Animals were tested at the end of the treatment period in 12 consecutive daily sessions: 8 acquisition sessions (platform submerged), followed by 4 cued sessions (platform visible). All trials were videotaped with a camera located 2 m above the water level. A SMART computerized tracking system (Panlab S. A., Barcelona, Spain) was used to analyze the mouse trajectories, measure escape latency, distance traveled, and swimming speed for each animal in each trial.
Training Sessions In the acquisition sessions (S1-S8), the platform was hidden 1 cm below the water level. From one daily session to the next, the platform was placed in a different location (E, SW, center, and NW); each position was used once every four consecutive daily sessions. Each of the 8 acquisition and 4 cued sessions (one session per day) consisted of four pairs of trials, 30-45 min apart. For each trial pair, the mice were randomly started from one of four positions (N, S, E, W), which was held constant for both trials. The first trial of a pair was terminated when the mouse located the platform or when 60 s had elapsed; the second trial commenced following a period of 20 s, during which the animal was allowed to stay on the platform. Several fixed cues outside of the maze were constantly visible from the pool.
Cued Sessions During the cued sessions the platform was visible: the water level was 1 cm below the platform, and its position was indicated with a flag. Eight trials were performed during each session, following the same experimental procedure as in the acquisition sessions. As shown in FIG. 7, all groups of mice learned the platform position throughout the acquisition sessions since they reduced the latency to reach the platform (ANOVA 'session': $F(7,65)=26.8$, $p<0.001$).

Figure 8:
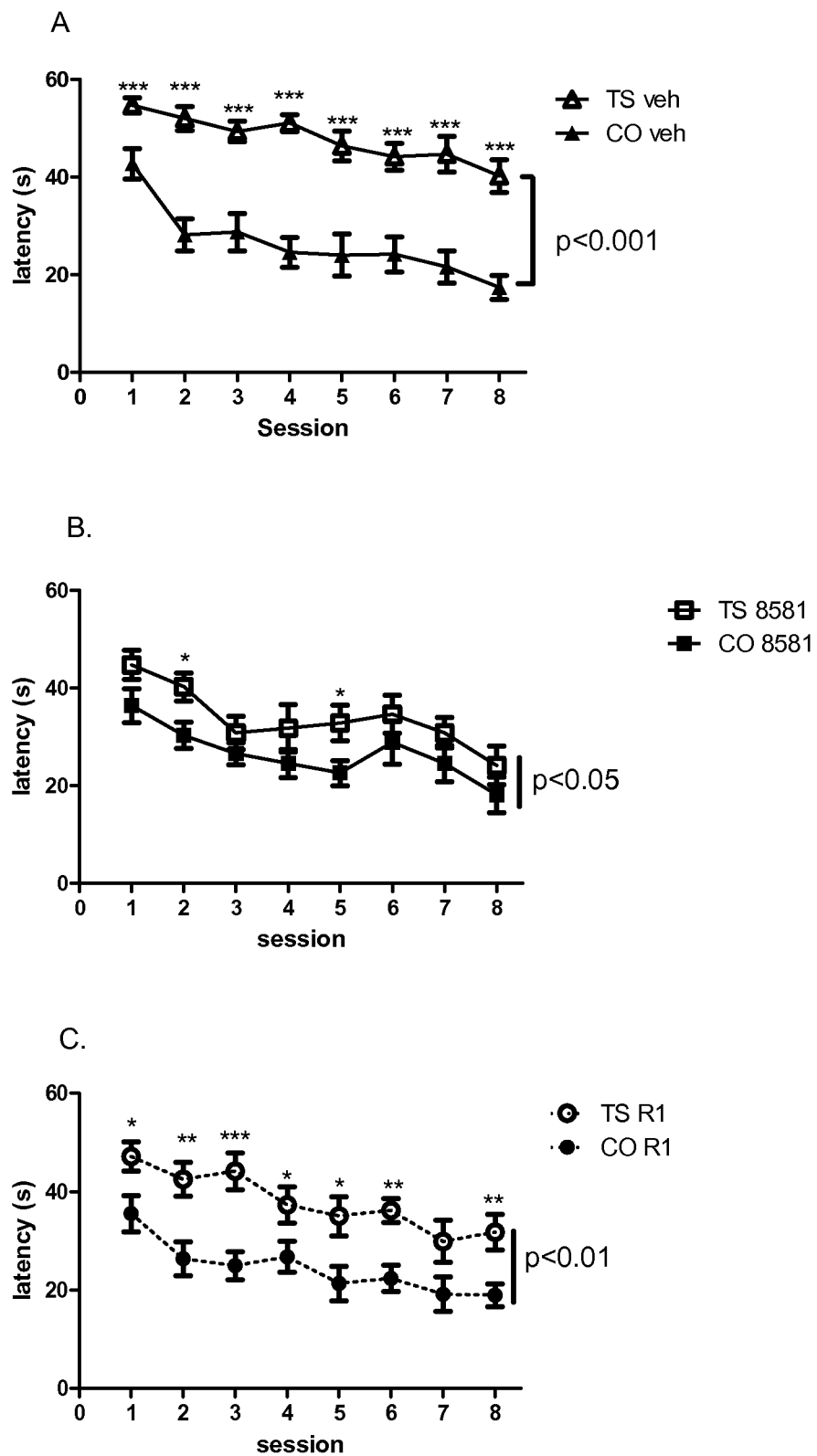
FIG. 8. Mean±S.E.M. of the latency to reach the platform during the eight acquisition sessions by Ts65Dn and control vehicle- (A) 8581- (B) and R1- treated mice and by vehicle and 8581-treated Ts65Dn (C) and control (D) mice. *: $p<0.05$; : $p<0.01$; *: $p<0.001$ T-test after significant ANOVAs.

Ts65Dn mice showed a pronounced learning deficit in the MWM (ANOVA 'genotype': $F(1,65)=39.26$, $p<0.001$; FIG. 8A), but the difference between Ts65Dn and control learning curves was reduced after 8581 (ANOVA 'genotype': $F(1,18)=4.69$, $p<0.05$; FIG. 8B) and after R1 treatment (ANOVA 'genotype': $F(1,26)=13.57$, $p<0.01$).

Figure 9:
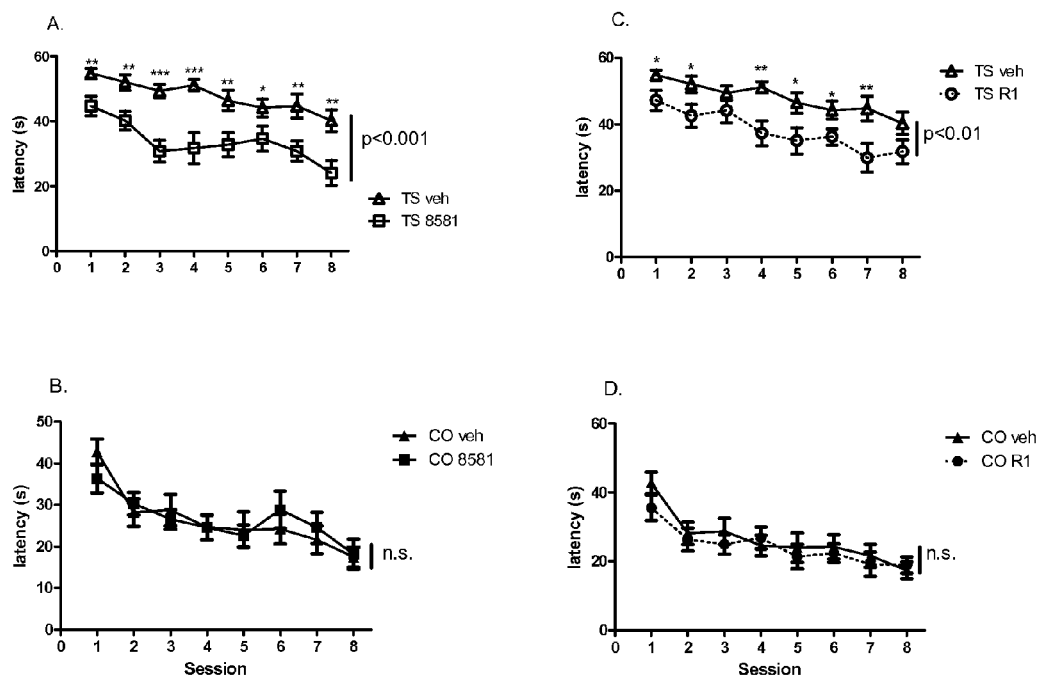
FIG. 9. Mean±S.E.M. of the latency to reach the platform during the eight acquisition sessions by vehicle and 8581-treated Ts65Dn (A) and control (B) mice and by vehicle and R1-treated Ts65Dn (C) and control (D) mice. *: $p<0.05$; : $p<0.01$; *: $p<0.001$ t-test after significant ANOVAs.

As shown in FIG. 9A, 8581-treatment significantly improved Ts65Dn mice performance (ANOVA 'treatment': $F(1,24)=32.43$, $p<0.001$). Chronic R1 treatment also improved Ts65Dn mice cognition ($F(1,24)=9.2$, $p<0.01$; FIG. 9C). 8581 (FIG. 9B) or R1 (FIG. 9D) did not significantly affect control mice performance.

Figure 10:
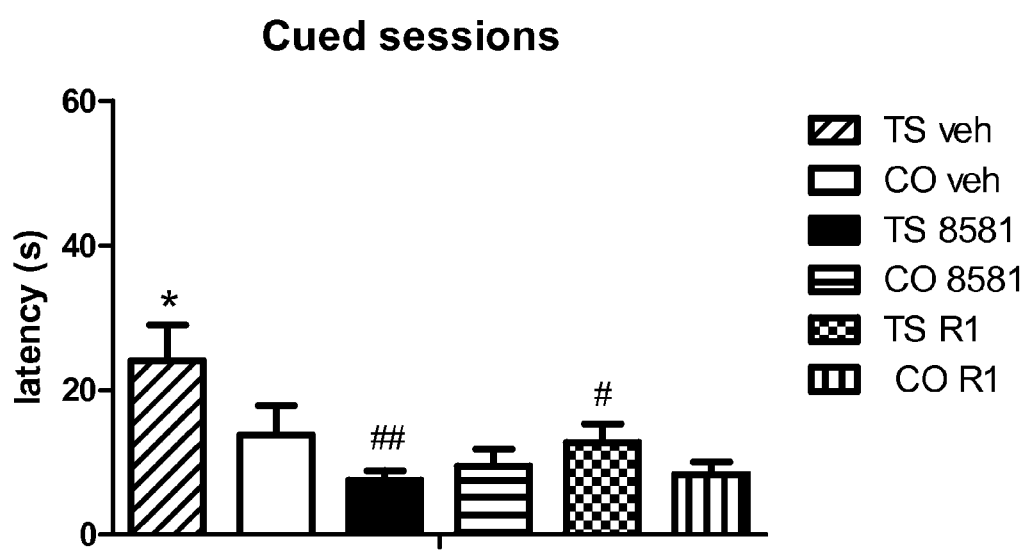
FIG. 10. Mean±S.E.M. of the latency to reach the platform during the cued sessions. *: $p<0.05$ Ts65Dn vs. control; #: $p<0.05$; ##: $p<0.01$ 8581 and R1 vs. vehicle.

During the cued sessions (FIG. 10), vehicle-treated Ts65Dn mice showed an increased latency to reach the platform with respect to control mice (ANOVA 'genotype': $F(1,46)=5.35$, $p=0.024$). R1 and 8581 treatment reduced the latency to reach the platform (ANOVA 'treatment': $F(1,46)=6.52$, $p=0.003$) in Ts65Dn but not in control mice (ANOVA 'genotype×treatment': $F(1,46)=3.44$, $p=0.038$)

Example 7

Long Term Potentiation (LTP)

The effect of chronic administration of 8581 and R1 on LTP was evaluated in the Ts65Dn mouse model of Down syndrome. 8581, R1 (20 mg/kg p.o.) or vehicle was administered for six weeks. Mice were decapitated 1 hour after the last administration and the brains were rapidly removed. The hippocampi were dissected and 400-μm slices were cut with a tissue chopper. Slices were allowed to recover for at least 1 hour in an interface chamber at RT with artificial cerebral spinal fluid (ACSF) containing (in mM): 120 NaCl, 3.5 KCl, 2.5 $CaCl_2$, 1.3 $MgSO_4$, 1.25 $NaH_2PO_4$, 26 $NaHCO_3$ and 10 D-glucose, saturated with 95% $O_2$ and 5% $CO_2$. Field excitatory postsynaptic potentials (fEPSPs) were recorded from the CA1 stratum radiatum with a glass micropipette (1-4 MΩ) containing 2 M NaCl and evoked by stimulation of the Schaffer collaterals with insulated bipolar platin/iridium electrodes >500 μm away from the recording electrode. The stimulus strength was adjusted to evoke fEPSPs equal to 50% of the relative maximum amplitude without superimposed population spike. After stable baseline recordings (100 μs pulse-duration, 0.033 Hz), long term potentiation (LTP) was induced by TBS (10 trains of 5 pulses at 100 Hz and intervals of 200 ms). The duration of the stimulation pulses was doubled during the tetanus. After 20 min of baseline recording, LTP was induced and recorded for 80 min in each individual hippocampal slice. Signals from recording electrodes were amplified and bandpass-filtered (1 Hz-1 kHz) and stored in a computer using the Spike 2 program (Spike2, Cambridge Electronic Design, Cambridge, UK). For the analysis, fEPSP slopes were expressed as a percentage of the baseline values recorded. Results from several slices were expressed as mean±SEM. The statistical analysis was carried out by repeated-measures (RM) MANOVA ('time'×'treatment'× 'genotype'). All the analyses were done using SPSS for Windows version 18.0.

Figure 11:
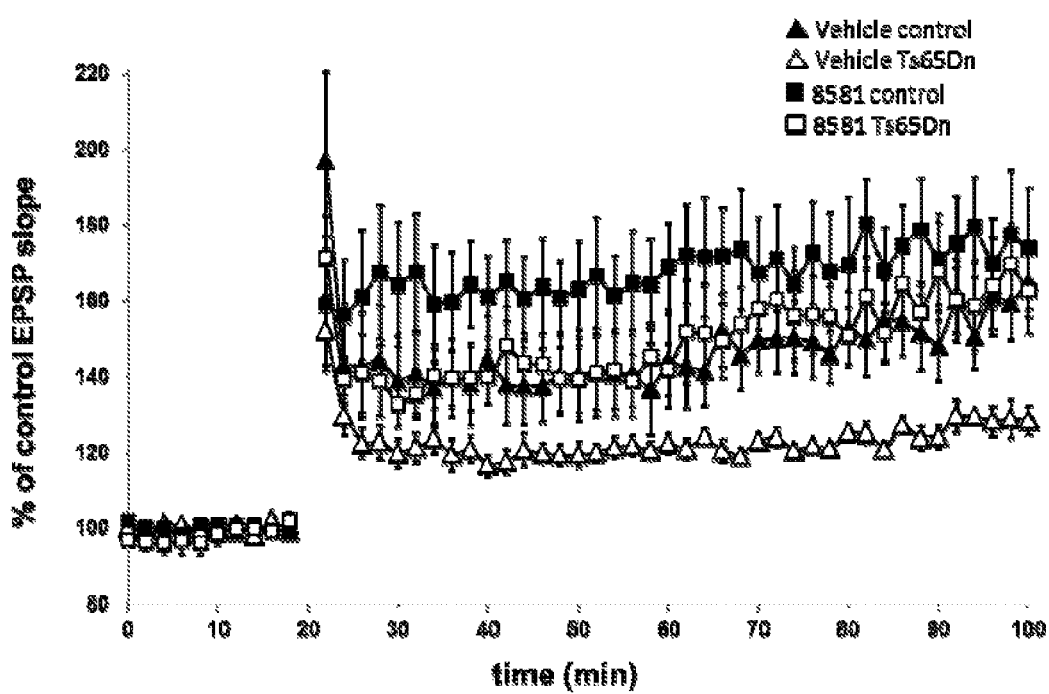
FIG. 11. 8581 reverses the deficit in Long-term potentiation in hippocampal slices of Ts65Dn mice after chronic treatment. Data are presented as means±S.E.M. of evoked EPSP recorded from hippocampal slices of vehicle, 8581 treated Ts65Dn (TS) and control (CO) mice. After a 20 min stable baseline period, tetanic stimulation was applied to hippocampal slices to induce LTP. Field ESPS slopes were normalized and presented as mean±SEM (n=5-7/group). * $p<0.05$ vs. vehicle (V).
Figure 12:
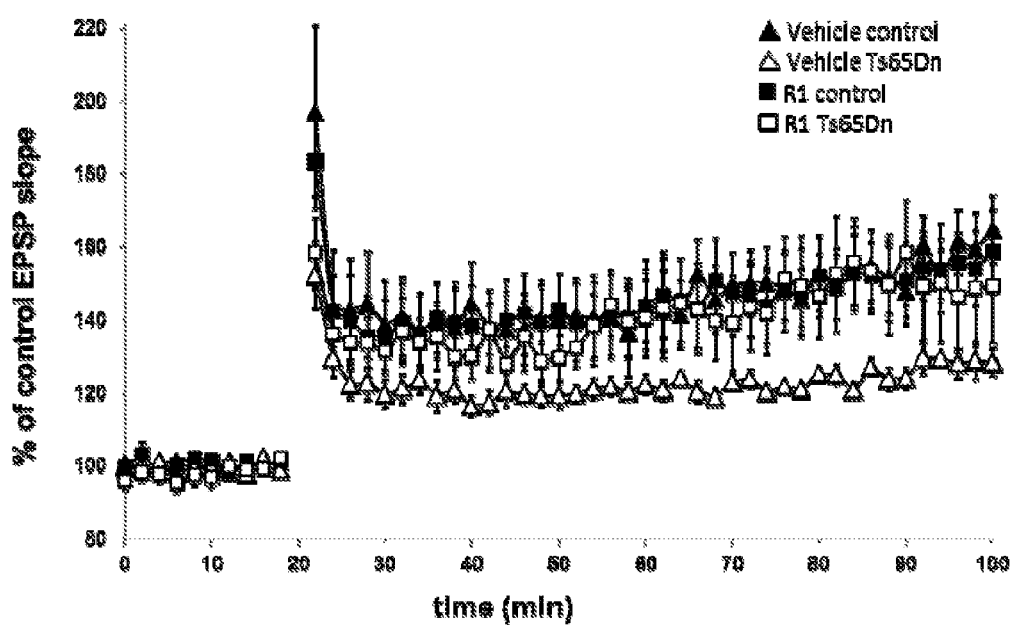
FIG. 12. $R^1$ reverses the deficit in Long-term potentiation in hippocampal slices of Ts65Dn mice after chronic treatment. Data are presented as means±S.E.M. of evoked EPSP recorded from hippocampal slices of vehicle, R1 treated TS and CO mice. After a 20 min stable baseline period, tetanic stimulation was applied to hippocampal slices to induce LTP. Field ESPS slopes were normalized and presented as mean±SEM (n=5-7/group). * $p<0.05$ vs. vehicle (V).

As shown in FIGS. 11 and 12, hippocampal slices of vehicle treated Ts65Dn mice displayed deficits in LTP. In contrast, the LTP induced in hippocampal slices of 8581 or R1 treated animals was not different from that induced in hippocampal slices of control mice (FIGS. 11 and 12 respectively). This suggests that chronically treating Ts65Dn mice with 8581 or R1 rescue the deficit in LTP probably by reducing the excessive GABA-mediated inhibition observed in these animals.

Example 8

Rescued Neurogenesis

Figure 13:
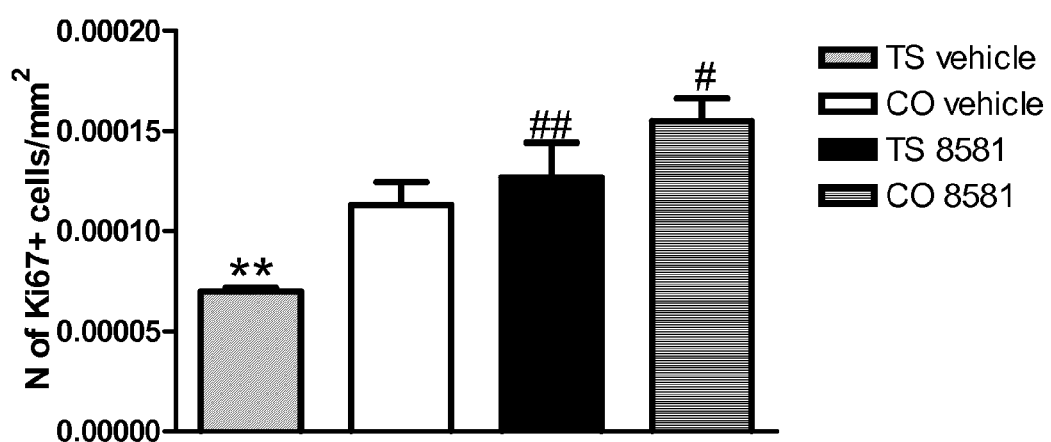
FIG. 13. 8581 rescues neuronal proliferation in the hippocampus of TS and CO mice. Data are expressed as means±S.E.M. of the density of Ki67+ cells in vehicle- and 8581-treated TS and CO mice. ANOVA 'genotype': $F(1, 20)=7.39$, $p=0.024$; 'treatment': $F(1,20)=6.30$, $p=0.033$; 'genotype×treatment': $F(1,20)=1.81$, $p=0.21$. \*\*: $p<0.01$ TS vs. CO; #: $p<0.05$, ##: $p<0.01$ vehicle vs. 8581-treated mice; Bonferroni tests after significant ANOVAs.
Figure 14:
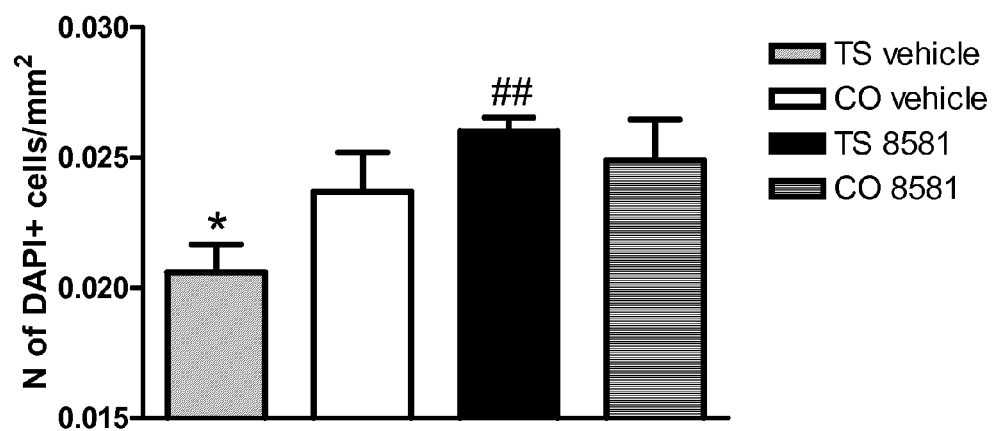
FIG. 14. 8581 rescued granular cell density in the hippocampus of TS mice. Data are expressed as means±S.E.M. of the density of DAPI+ cells in the granular cell layer of vehicle- and 8581-treated TS and CO mice (A). ANOVA 'genotype': $F(1, 20)=0.51$, $p=0.49$; 'treatment': $F(1,20)=7.09$, $p=0.026$; 'genotype×treatment': $F(1,20)=4.00$, $p=0.076$. \*: $p<0.05$ TS vs. CO; ##: $p<0.01$ vehicle vs. 8581-treated mice; Bonferroni tests after significant ANOVAs. (B) Representative images of DAPI immunostaining of vehicle- and 8581-treated TS and CO mice.
Figure 14:
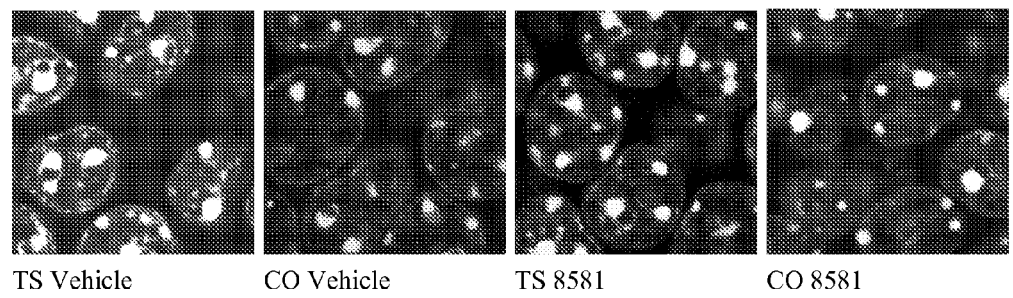

Alterations in hippocampal morphology such as reductions in granule cell density and hippocampal neurogenesis have also been implicated in the learning deficits shown by Ts65Dn mice. Spatial learning is known to depend on the functional integrity of the hippocampus, a structure that plays a key role in information encoding and retrieving in the CNS. We have studied the population of newborn cells in the dentate girus (DG) by labelling proliferating cells with anti-Ki67, a marker of cells undergoing the late G1 phase and phases G2 and M. We confirmed that hippocampal neurogenesis was reduced in these mice and showed that chronic administration of 8581 completely restored the density of proliferating cells in TS mice (p=0.033; FIG. 13). Also, neuronal survival of the cells that have undergone maturation was also normalized in TS mice, as shown by the increase in DAPI+ cells found in TS mice after chronic 8581 administration (p=0.026; FIG. 14).

Therefore, this compound facilitates cell proliferation and survival of neurons that have undergone maturation. Since both new-born neurons and mature neurons seem to be implicated in hippocampus-dependent learning and memory, the restoration of proliferation and of the density of mature neurons is likely to be implicated in the cognitive-enhancing effects of 8581 in TS mice.

Figure 15:
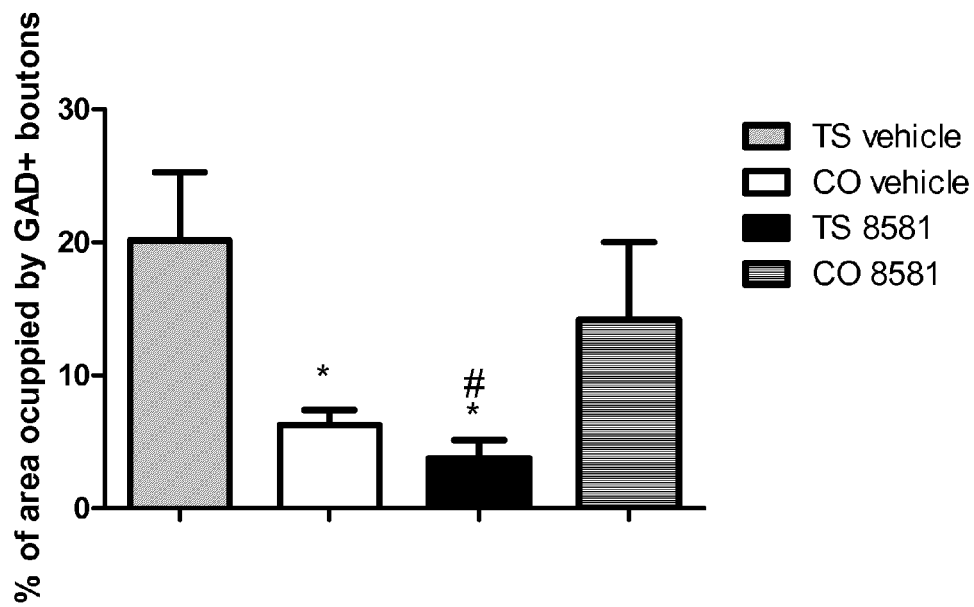
FIG. 15. 8581 normalized the percentage of area occupied by GAD+ buttons in the hippocampus of TS mice. Data are expressed as means±S.E.M. of the percentage of area occupied by GAD+ buttons in the hippocampus of vehicle- and 8581-treated TS and CO mice (A). ANOVA 'genotype': $F(1, 20)=0.085$, $p=0.77$; 'treatment': $F(1,20)=1.14$, $p=0.30$; 'genotype×treatment': $F(1,20)=7.15$, $p=0.017$. \*: $p<0.05$ TS vs. CO; #: $p<0.05$ vehicle vs. 8581-treated mice; Bonferroni tests after significant ANOVAs. (B) Representative images of GAD immunostaining of vehicle- and R04938581-treated TS and CO mice.
Figure 15:
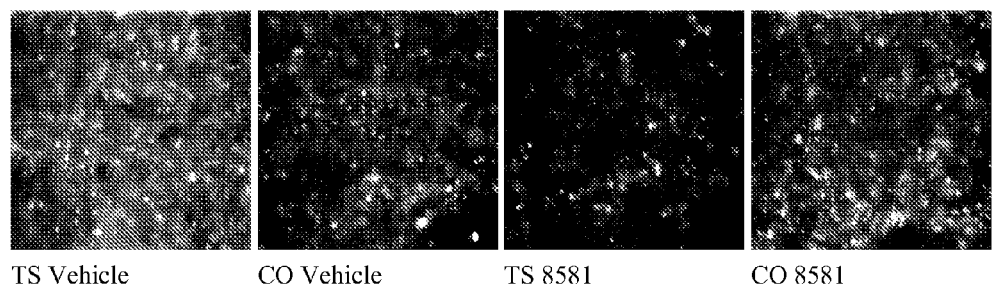

In addition, we found that in TS mouse hippocampus there is an enhancement in the number of GABAergic synapses compared to control animals. Importantly chronic treatment with 8581 rescue this alteration as the number of GAD positive boutons decreased dramatically after chronic treatment with this selective GABAA α5 NAM (p=0.017; FIG. 15). This treatment produced a non-significant tendency to increase the number of these synapses in CO mice.

Example 9

Figure 16:
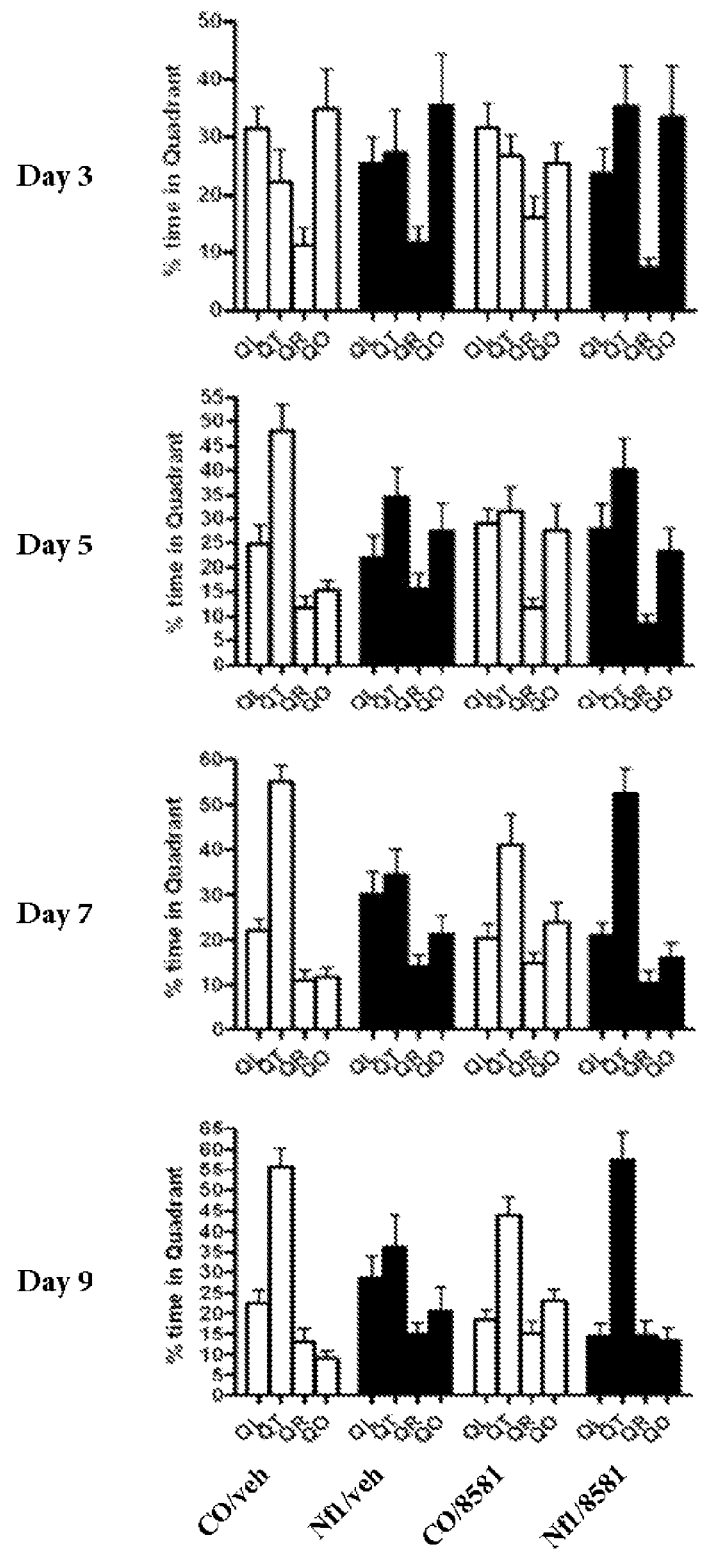
FIG. 16. 8581 (1 mg/kg) rescues spatial learning deficits of Nf1+/− mice. Mean percentage of time spent in each quadrant during a probe trial (QL: left to target quadrant; QT: target quadrant; QR: right to target quadrant; QO: opposite to target quadrant).
Figure 17:
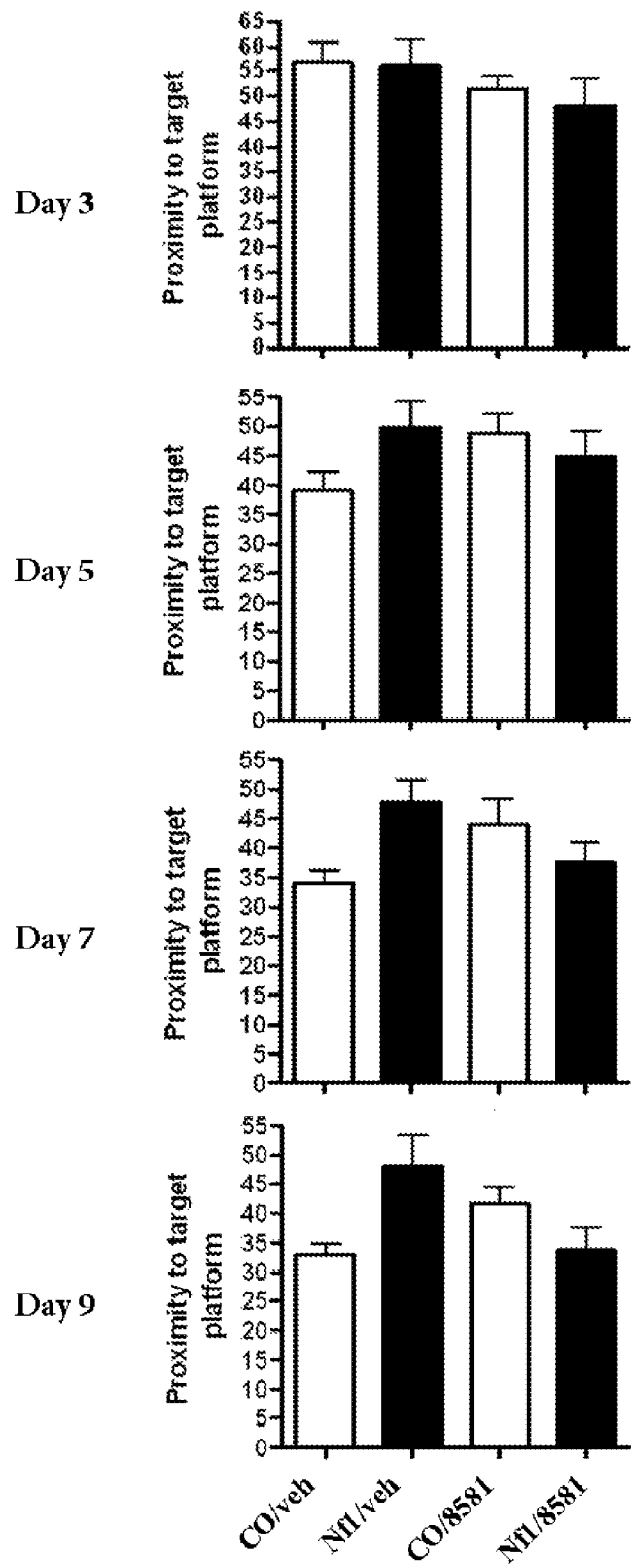
FIG. 17. 8581 (1 mg/kg) rescues spatial learning deficits of Nf1+/− mice. Average proximity to the target platform during a probe trial.

Spatial Learning of Nf1+/− Mice in the Morris Water Maze 1 week after handling, mice were trained with two consecutive trials per day for 8-9 days 30 minutes after i.p. injection of 8581 or vehicle. In each trial, mice were given 60 s to find the platform. After each trial, mice were put on the platform for 15 s. On the day of probe trial (Day 3, Day 5, Day 7, and Day 9) 60 s of probe trial was performed after training. On probe trial 1 (day 3), none of the groups tested learned to search specifically in the target quadrant; probe trials 3 and 4 (days 7 and 9) showed that the Nf1/veh group was significantly impaired compared to CO/veh (two-way ANOVA, quadrant×genotype interaction, $F(3,51)=5.662$, $P<0.01$). Importantly, 8581-treated Nf1+/− mice show comparable performance to control animals on all the probe trials, suggesting that 8581 rescued the spatial learning deficits of Nf1+/− mice. Two different measures of spatial learning (% search in quadrant (FIG. 16) and average proximity to the target platform (FIG. 17)) show similarly, that active pharmaceutical compounds used in present invention rescue spatial learning deficits of Nf1+/− mice (CO/veh (n=10), Nf1/veh (n=9), CO/8581 (n=10), and Nf1/8581 (n=11)).

Figure 18:
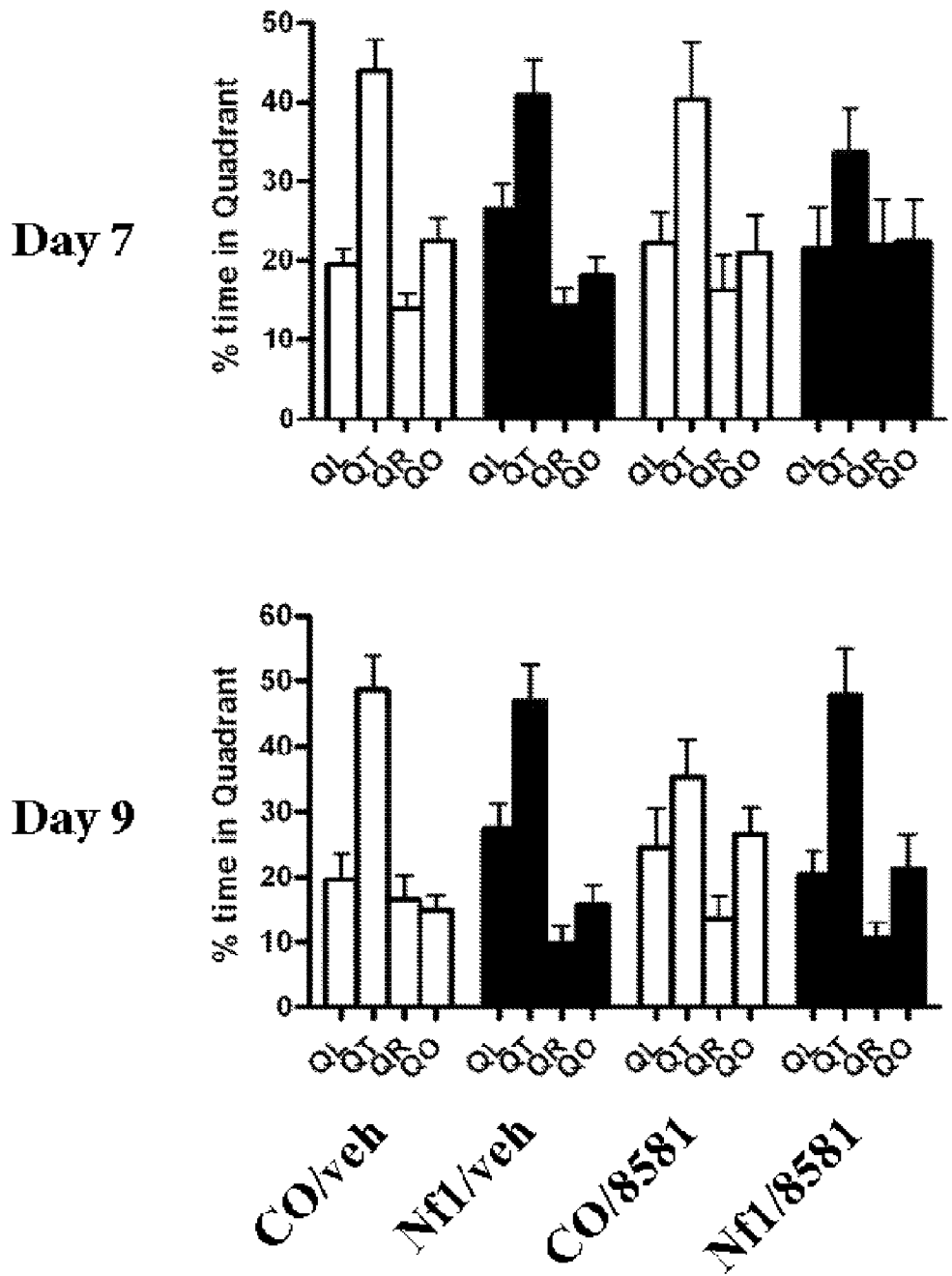
FIG. 18. 8581 (1 mg/kg) does not affect the performance of Nf1+/− mice under conditions that occlude their behavioral deficits. Mean percentage of time spent in each quadrant during a probe trial (QL: left to target quadrant; QT: target quadrant; QR: right to target quadrant; QO: opposite to target quadrant).
Figure 19:
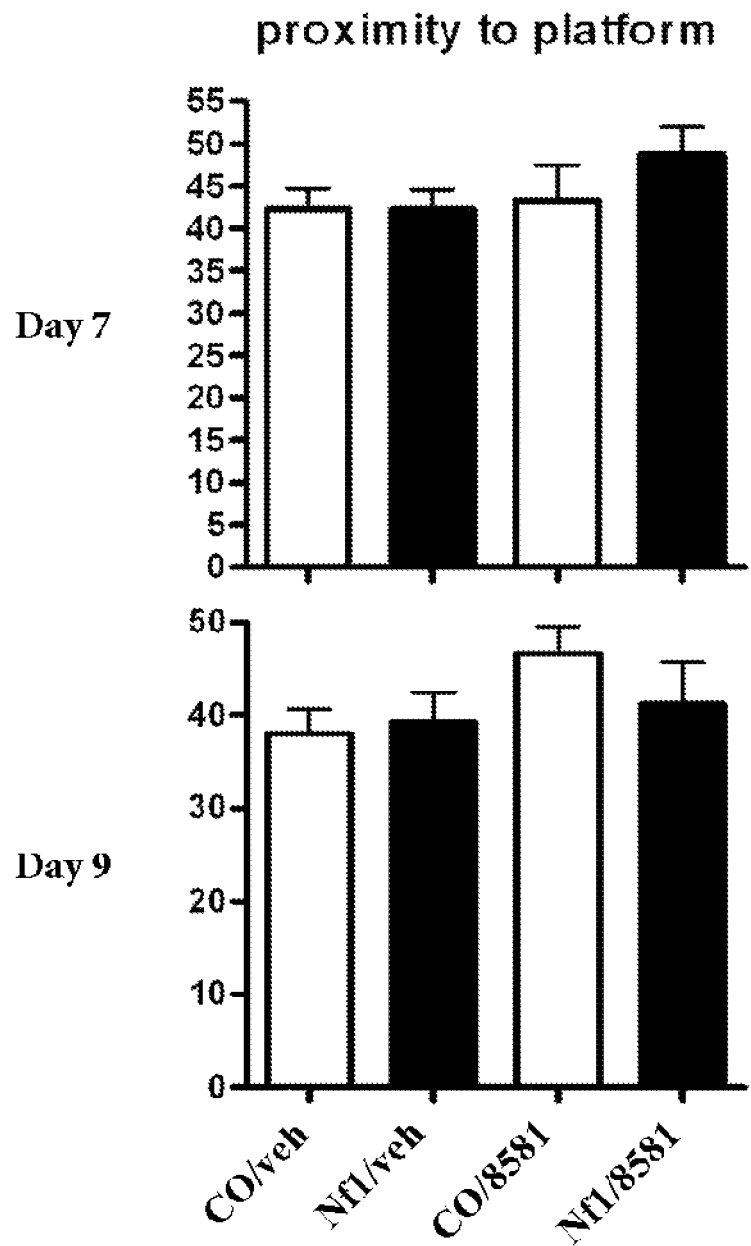
FIG. 19. 8581 (1 mg/kg) does not affect the performance of Nf1+/− mice under conditions that occlude their behavioral deficits. Average proximity to the target platform during a probe trial.

Effects of active pharmaceutical compounds used in present invention on the performance of Nf1+/− mice were tested under conditions in which the spatial learning of the mutants was indistinguishable from controls (less extinction due to lower number of probe trials). Mean percentage of time spent in each quadrant during a probe trial in plotted in FIG. 18. Average proximity to the target quadrant is plotted in FIG. 19. Results show that Nf1+/− mice treated with vehicle were indistinguishable from control mice similarly treated. Comparisons between % search on target quadrant and proximity to target quadrant did not reveal any difference between groups. On probe trial 1 and 2 (days 5 and 7), all groups searched selectively in the target quadrant (p<0.01), and there were no differences between groups.

Example 10

Fear Conditioning

Figure 20:
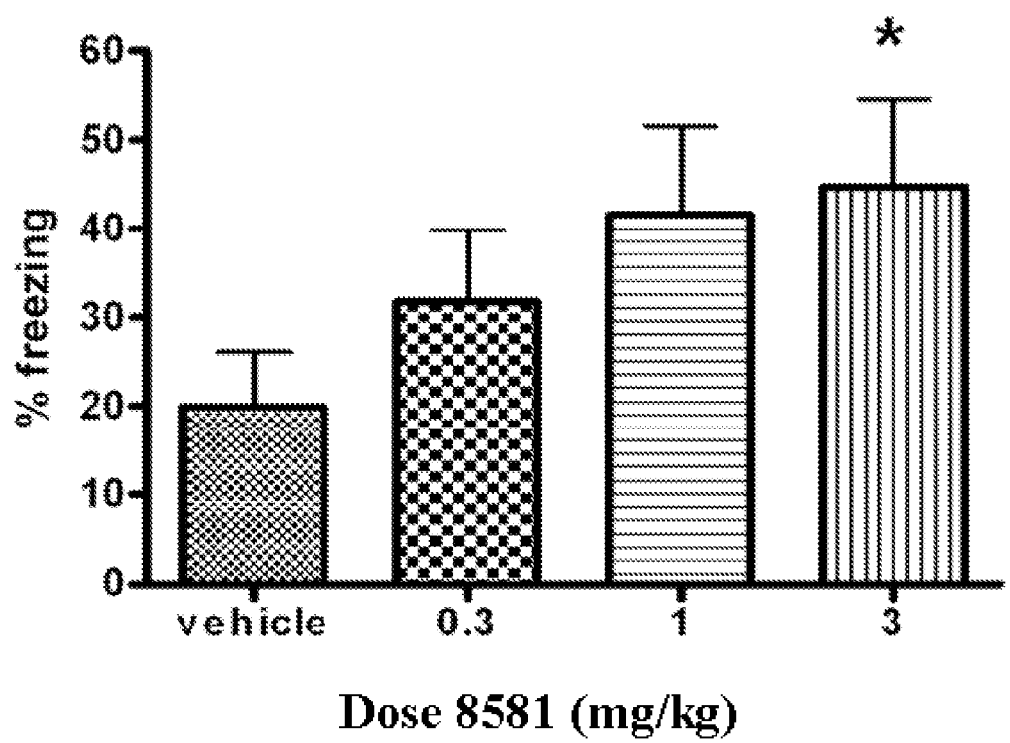
FIG. 20. Contextual conditioning: Dose response curve (0.3, 1.0 and 3.0 mg/kg) of control mice treated with 8581 ($P<0.05$).
Figure 21:
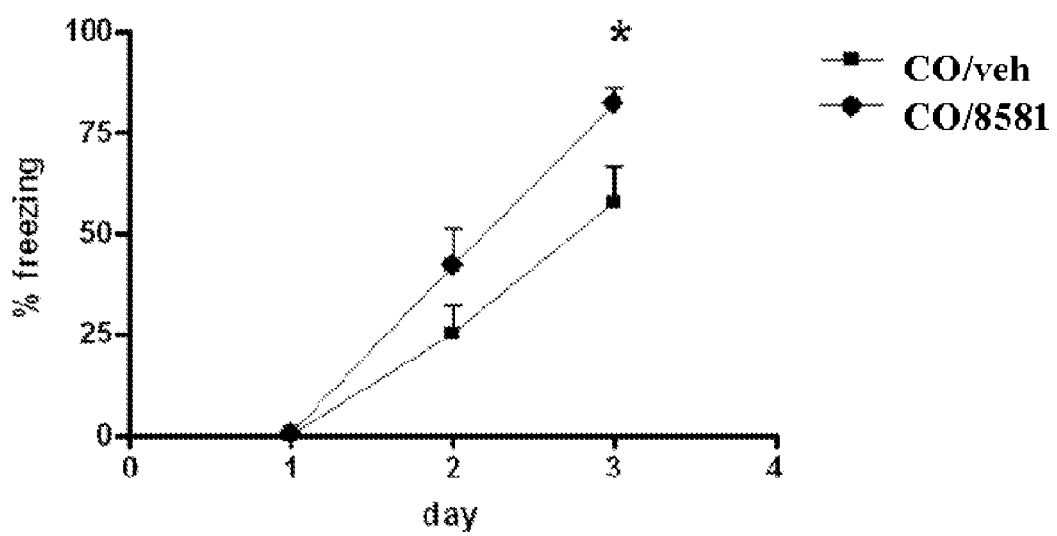
FIG. 21. Contextual conditioning of control mice when given 8581 (1 mg/kg) for two consecutive days.

Control mice (B16;129F1) were trained with a contextual fear-conditioning protocol using either one trial per day for one day (FIG. 20) or two consecutive days (FIG. 21). On the training day, 30 minutes after i.p. injection of 8581 or vehicle, mice were placed in training chamber. A foot shock (1 s, 0.4 mA) was delivered 40 s after placement. Conditioned response (percentage freezing time of the mice) was recorded 24 h after training by using automated procedures. Average freezing levels during the first 30 s of each training day and 24 hr after the last training trial were plotted.

The dose response curve (0.3, 1.0 and 3.0 mg/kg) as shown in FIG. 20 reveals a dose-dependent increase in contextual fear conditioning in control mice. 3 mg/kg 8581 significantly enhanced freezing at 24 hr after training (p<0.05). As can be seein from FIG. 21, 1 mg/kg 8581 also caused a significant increase in contextual conditioning when mice were trained for two consecutive days. Mice treated with the drug freeze significantly more compared to control/vehicle group ($F(1, 18)=5.254$, $p=0.034$).

Example 11

Rotarod

Figure 22:
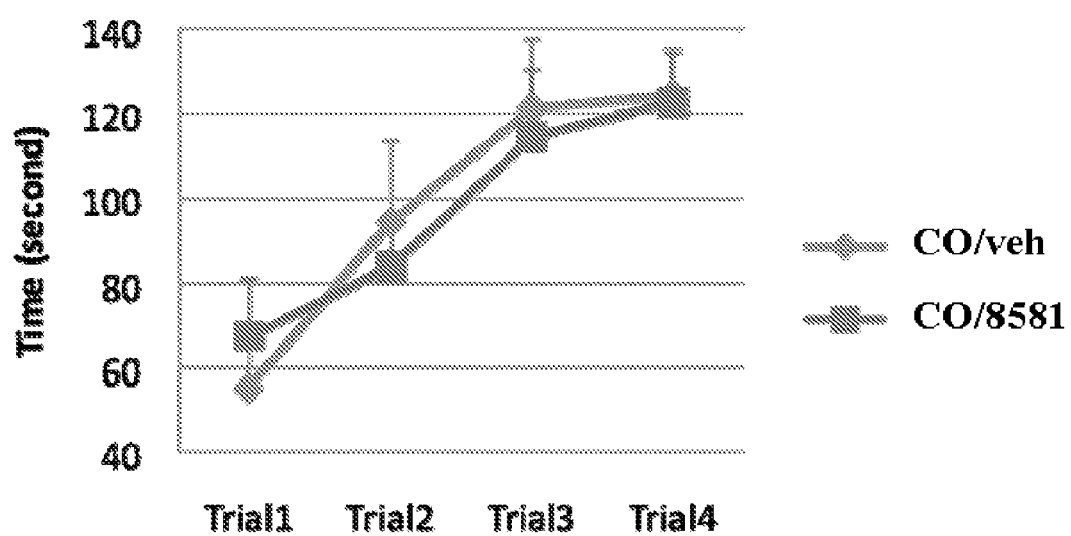
FIG. 22. Performance of control mice treated with vehicle or 8581 (1 mg/kg) in the Rotarod.
Figure 23:
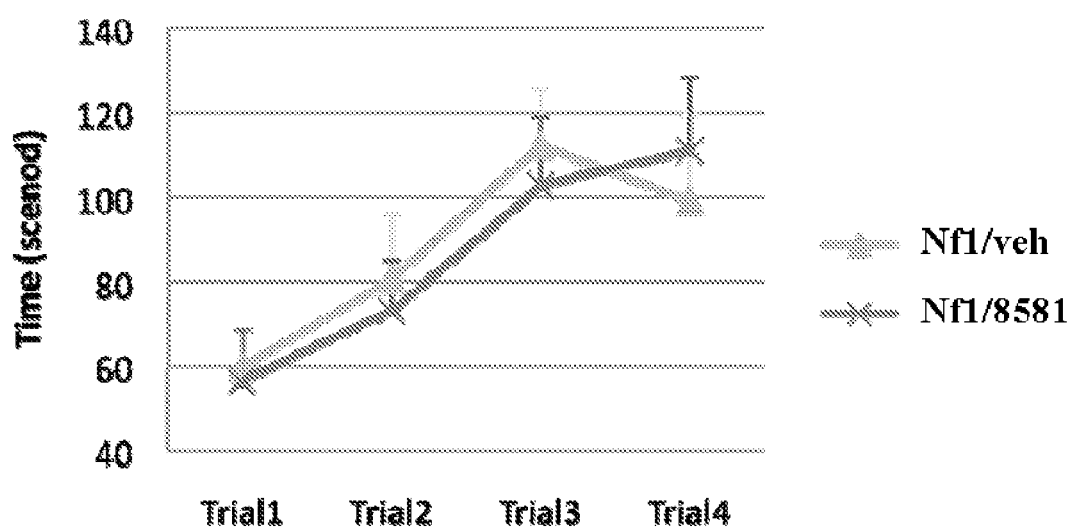
FIG. 23. Performance of Nf1+/− mice treated with vehicle or 8581 (1 mg/kg) in the Rotarod.

Control mice (B16;129F1) and Nf1+/− mice were treated with vehicle or with 8581 (n=10 for each of the 4 groups). 30 minutes after i.p. injection of 8581 (1 mg/kg) or vehicle, mice were tested with a rotarod protocol using accelerating speeds (4-40 rpm, maximal duration 300 s) for four trials with 30 min intertrial interval. FIG. 22 visualizes performance of control mice in the Rotarod and FIG. 23 illustrates the performance of Nf1+/− mice in the Rotarod. 8581 did not affect the performance of either Nf1+/− mutant or control mice.

TABLE 1

|  | Control | Ts65Dn |
|---|---|---|
| 8581 | 10 | 10 |
| R1 | 16 | 15 |
| Vehicle | 13 | 13 |

TABLE 2a

| Compound | hKi α5 [nM] | hKi α1 [nM] | hKi α2 [nM] | hKi α3 [nM] | hKi α1/ hKi α5 | hKi α2/ hKi α5 | hKi α3/ hKi α5 |
|---|---|---|---|---|---|---|---|
| 8580 | 9.1 | 43.9 | 25.4 | 26.2 | 5 | 3 | 3 |
| 8581 | 4.6 | 174.3 | 185.4 | 79.6 | 38 | 40 | 17 |
| 8582 | 16.5 | 256.5 | 246.3 | 105.8 | 16 | 15 | 6 |
| 8583 | 1.6 | 28.3 | 13.9 | 10.5 | 18 | 9 | 7 |
| 8584 | 2.5 | 125.3 | 181.0 | 116.7 | 50 | 72 | 47 |
| 8585 | 0.3 | 3.8 | 1.5 | 0.7 | 14 | 5 | 2 |
| 8586 | 2.1 | 15.3 | 23.7 | 14.0 | 7 | 12 | 7 |
| 8587 | 10.9 | 249.8 | 141.4 | 105.8 | 23 | 13 | 10 |
| 8588 | 1.1 | 20.5 | 40.1 | 16.0 | 19 | 37 | 15 |
| 8589 | 6.1 | 225.9 | 228.7 | 215.8 | 37 | 37 | 35 |
| 8590 | 0.5 | 2.1 | 3.7 | 3.9 | 4 | 7 | 8 |
| 8591 | 7.1 | 624.0 | 668.6 | 515.4 | 88 | 94 | 73 |
| O1 | 1.3 | 504.3 | 100.5 | 110.2 | 388 | 77 | 85 |
| P1 | 29.9 |  |  |  |  |  |  |
| Q1 | 15.1 | 633.0 | 437.9 | 399.6 | 42 | 29 | 26 |
| R1 | 4.7 | 984.6 | 501.5 | 489.1 | 209 | 107 | 104 |
| S1 | 5.4 | 550.8 | 209.3 | 220.2 | 102 | 39 | 41 |
| T1 | 14.6 | 467.9 | 292.8 | 387.1 | 32 | 20 | 27 |
| U1 | 0.3 | 45.8 | 7.2 | 7.5 | 153 | 24 | 25 |
| V1 | 1.2 | 143.3 | 53.3 | 76.1 | 119 | 44 | 63 |
| W1 | 0.4 | 34.6 | 10.7 | 17.7 | 87 | 27 | 44 |

TABLE 2b

| Compound | Efficacy [%] GABA A α5β3γ2 | Efficacy [%] GABA A α1β2/3γ2 | Efficacy [%] GABA A α2β3γ2 | Efficacy [%] GABA A α3β3γ2 |
|---|---|---|---|---|
| 8580 | −35 | | | |
| 8581 | −46 | −1 | −11 | −1 |
| 8582 | −37 | −21 | | |
| 8585 | −41 | −37 | | |
| 8586 | −33 | −5 | +2 | +7 |
| 8587 | −42 | −28 | | |
| 8591 | −31 | +4 | −7 | +23 |
| O1 | −50 | −19 | −34 | −43 |
| Q1 | −35 | −11 | −18 | −17 |
| R1 | −39 | −4 | −6 | −2 |
| T1 | −31 | −3 | +5 | +9 |
| U1 | −33 | −15 | −34 | −21 |
| V1 | −33 | 0 | +9 | +16 |

TABLE 3

| | Vehicle | | 8581 | | R1 | | MANOVA 'genotype x treatment' | | |
|---|---|---|---|---|---|---|---|---|---|
| | | | | | | | genotype | treatment F | gen x treat- |
| | Ts65Dn | control | Ts65Dn | control | Ts65Dn | control | F (1.76) | (2.76) | ment |
| Vision | 8.23 ± 0.60 | 8.54 ± 0.57 | 7.67 ± 0.88 | 7.64 ± 0.47 | 9.19 ± 0.54 | 8.40 ± 0.52 | 0.09, p = 0.76 | 1.74, p = 0.18 | 0.53, p = 0.58 |
| Auditory startle | 1.15 ± 0.19 | 1.31 ± 0.24 | 1.33 ± 0.17 | 1.00 ± 0.13 | 1.31 ± 0.18 | 1.00 ± 0.20 | 1.07, p = 0.30 | 0.10, p = 0.90 | 0.92, p = 0.40 |
| Righting reflex | 3.00 ± 0.00 | 3.00± 0.00 | 3.00 ± 0.00 | 3.00 ± 0.00 | 3.00 ± 0.00 | 3.00 ± 0.0 | | | |
| Grip strength | 1.62 ± 0.24 | 2.00 ± 0.28 | 2.00 ± 0.24 | 1.55 ± 0.21 | 1.75 ± 0.19 | 2.2 ± 0.22 | 0.74, p = 0.39 | 0.63, p = 0.53 | 2.33, p = 0.10 |
| Equilibrium wooden bar | 3.08 ± 0.37 | 2.4 ± 0.24 | 3.55 ± 0.38 | 2.8 ± 0.38 | 3.19 ± 0.31 | 2.53 ± 0.24 | 7.58, p = 0.008 | 0.80, p = 0.45 | 0.02, p = 0.97 |
| Latency to fall wooden bar | 20.0 ± 0.0 | 19.8 ± 0.19 | 17.77 ± 2.22 | 20.00 ± 0.00 | 20.00 ± 0.0 | 20.00 ± 0.0 | 1.62, p = 0.20 | 1.62, p = 0.20 | 1.89, p = 0.15 |
| Equilibrium aluminium bar | 2.31 ± 0.54 | 1.38 ± 0.43 | 1.00 ± 0.44 | 1.36 ± 0.45 | 1.13 ± 0.33 | 0.80 ± 0.34 | 0.50, p = 0.48 | 2.09, p = 0.13 | 0.80, p = 0.45 |
| Latency to fall aluminium bar | 15.15 ± 1.55 | 13.42 ± 1.33 | 12.11 ± 2.07 | 14.73 ± 1.27 | 13.71 ± 1.32 | 11.16 ± 1.57 | 0.10, p = 0.74 | 0.64, p = 0.52 | 1.39, p = 0.25 |
| Prehensile reflex | 2.92 ± 0.83 | 2.69 ± 0.17 | 2.67 ± 0.24 | 2.45 ± 0.31 | 2.75 ± 0.17 | 2.53 ± 0.22 | 1.63, p = 0.20 | 0.67, p = 0.51 | 0.00, p = 1.00 |
| Traction capacity | 2.67 ± 0.62 | 2.31 ± 0.63 | 1.67 ± 0.62 | 1.82 ± 0.55 | 2.50 ± 0.57 | 1.80 ± 0.45 | 0.39 p = 0.53 | 0.72, p = 0.48 | 0.25, p = 0.77 |
| Number of crossings coat hanging | 3.67 ± 0.34 | 3.62 ± 0.96 | 3.33 ± 0.50 | 2.64 ± 0.43 | 3.19 ± 0.73 | 2.73 ± 0.36 | 1.76, p = 0.18 | 1.36, p = 0.26 | 0.71, p = 0.49 |
| Latency arrival coat hanging | 32.42 ± 6.16 | 36.00 ± 5.62 | 35.44 ± 5.76 | 46.45 ± 5.79 | 37.37 ± 4.91 | 30.93 ± 5.16 | 0.34, p = 0.55 | 0.85, p = 0.42 | 1.22, p = 0.29 |

TABLE 4

| | Vehicle | | 8581 | | R1 | | MANOVA 'genotype x treatment' | | |
|---|---|---|---|---|---|---|---|---|---|
| | | | | | | | genotype | treatment | gen x treat- |
| | s65Dn | control | Ts65Dn | control | Ts65Dn | control | F(1.76) | (2.76) | ment |
| Crossings | 127.15** ± 11.86 | 79.00 ± 5.24 | 106.11 ± 9.80 | 73.27 ± 8.31 | 93.19 ± 7.50 | 72.13 ± 7.05 | 23.55, p < 0.001 | 3.27, p = 0.04 | 1.42, p = 0.24 |
| Rearings | 13.77 ± 2.55 | 11.54 ± 1.98 | 20.67 ± 5.69 | 17.73 ± 3.06 | 13.19 ± 2.20 | 13.86 ± 2.01 | 0.41, p = 0.52 | 2.77, p = 0.07 | 0.24, p = 0.78 |
| Number of Head-dippings | 22.62 ± 2.21 | 18.15 ± 1.84 | 18.22 ± 1.96 | 14.82 ± 2.00 | 20.50 ± 1.95 | 16.13 ± 1.71 | 6.18, p = 0.015 | 1.71, p = 0.18 | 0.03, p = 0.96 |
| Time exploring holes | 37.88 ± 7.55 | 33.92 ± 6.63 | 26.28 ± 4.17 | 30.43 ± 6.83 | 37.58 ± 5.07 | 28.28 ± 4.62 | 0.36, p = 0.54 | 0.68, p = 0.50 | 0.58, p = 0.56 |
| ABA index | 5.23 ± 0.60 | 3.23 ± 0.53 | 3.89 ± 0.72 | 2.64 ± 0.86 | 4.25 ± 0.72 | 4.06 ± 0.56 | 4.21, p = 0.044 | 1.10, p = 0.33 | 1.02, p = 0.36 |

TABLE 5

| Genotype | Dose (mg/kg) | | | |
|---|---|---|---|---|
| | 0.1 | | 1 | |
| | Nf1+/− | control | Nf1+/− | control |
| 0.5 h | 10.97 ± 1.73 | 9.45 ± 3.05 | 192 ± 35 | 271 ± 1 |
| 3 h | <0.5 | <0.5 | 8.945 ± 0.5 | 11.89 ± 2.51 |
| 7 h | <0.5 | <0.5 | <0.5 | <0.5 |
| 24 h | <0.5 | <0.5 | <0.5 | <0.5 |

The invention claimed is:

1. A method of treating or delaying the progression of central nervous system (CNS) conditions related to excessive GABAergic inhibition in the cortex and hippocampus comprising administering to a subject having such condition a therapeutically effective amount of a GABA A α5 negative allosteric modulator wherein the GABA A α5 negative allosteric modulator is (1,1-Dioxo-1,6-thiomorpholin-4-yl)-{6-[3-(4-fluoro-phenyl)-5-methyl-isoxazol-4-ylmethoxy]-pyridin-3-yl}-methanone,
or a pharmaceutically acceptable salt thereof, and
wherein said CNS condition is cognitive deficits in Down Syndrome.

2. The method of claim 1, wherein the excessive GABAergic inhibition in the cortex and hippocampus is caused by neurodevelopmental defects.

3. The method of claim 1, wherein the CNS conditions are caused by neurodevelopmental defects which result in excessive GABAergic inhibition in the cortex and hippocampus.

* * * * *